United States Patent
Egan et al.

(10) Patent No.: US 11,131,666 B2
(45) Date of Patent: *Sep. 28, 2021

(54) SYSTEM AND APPARATUS FOR POINT-OF-CARE DIAGNOSTICS

(71) Applicant: Quidel Corporation, San Diego, CA (US)

(72) Inventors: Richard L. Egan, Oceanside, CA (US); Michael Jon Hale, San Diego, CA (US); Jhobe Steadman, San Diego, CA (US)

(73) Assignee: Quidel Corporation, San Diego, CA (US)

( * ) Notice: Subject to any disclaimer, the term of this patent is extended or adjusted under 35 U.S.C. 154(b) by 64 days.

This patent is subject to a terminal disclaimer.

(21) Appl. No.: 16/297,503

(22) Filed: Mar. 8, 2019

(65) Prior Publication Data

US 2019/0271695 A1    Sep. 5, 2019

Related U.S. Application Data

(63) Continuation of application No. 14/932,769, filed on Nov. 4, 2015, now Pat. No. 10,281,462, which is a
(Continued)

(51) Int. Cl.
*G01N 33/543* (2006.01)
*G01N 33/53* (2006.01)
(Continued)

(52) U.S. Cl.
CPC .......... *G01N 33/54366* (2013.01); *B01L 9/52* (2013.01); *G01N 21/6428* (2013.01);
(Continued)

(58) Field of Classification Search
CPC ... G01N 21/6428; G01N 21/6486; B01L 9/52
See application file for complete search history.

(56) References Cited

U.S. PATENT DOCUMENTS

| 4,934,817 A | 6/1990 | Gassenhuber |
| 5,204,264 A | 4/1993 | Kaminer et al. |

(Continued)

FOREIGN PATENT DOCUMENTS

| CN | 2653511 Y | 11/2004 |
| CN | 1766580 A | 5/2006 |

(Continued)

OTHER PUBLICATIONS

Ahn et al., "Development of a point-of-care assay system for high-sensitivity C-reaction protein in whole blood", Clinica Chimica Acta, vol. 332. pp. 51-59 (2003).
(Continued)

*Primary Examiner* — Brian R Gordon
*Assistant Examiner* — Dwan A Gerido
(74) *Attorney, Agent, or Firm* — McDermott Will & Emery LLP; Judy M. Mohr; Brett A. Schweers

(57) ABSTRACT

A system comprised of an apparatus and a test device is described. The test device and the apparatus are designed to interact to determine the presence or absence of an analyte of interest in a sample placed on the test device.

14 Claims, 16 Drawing Sheets

Related U.S. Application Data continuation of application No. 13/783,019, filed on Mar. 1, 2013, now Pat. No. 9,207,181.

(60) Provisional application No. 61/666,689, filed on Jun. 29, 2012, provisional application No. 61/636,105, filed on Apr. 20, 2012, provisional application No. 61/605,694, filed on Mar. 1, 2012.

(51) Int. Cl.
*G01N 33/569* (2006.01)
*G01N 21/64* (2006.01)
*G01N 33/558* (2006.01)
*G01N 21/84* (2006.01)
*B01L 9/00* (2006.01)

(52) U.S. Cl.
CPC ..... *G01N 21/6486* (2013.01); *G01N 21/8483* (2013.01); *G01N 33/53* (2013.01); *G01N 33/558* (2013.01); *G01N 33/56944* (2013.01); *G01N 33/56983* (2013.01); *B01L 2300/0816* (2013.01); *B01L 2300/0825* (2013.01); *G01N 2021/6439* (2013.01); *G01N 2201/12707* (2013.01); *G01N 2201/12792* (2013.01); *G01N 2333/11* (2013.01); *G01N 2469/10* (2013.01)

(56) References Cited

U.S. PATENT DOCUMENTS

| | | | |
|---|---|---|---|
| 5,238,737 | A | 8/1993 | Burkhardt et al. |
| 5,414,258 | A | 5/1995 | Liang |
| 5,766,961 | A | 6/1998 | Pawlak |
| 5,770,460 | A | 6/1998 | Pawlak et al. |
| 6,074,616 | A | 6/2000 | Buechler et al. |
| 6,136,610 | A | 10/2000 | Polito et al. |
| 6,144,455 | A | 11/2000 | Tuunanen et al. |
| 6,267,722 | B1 | 7/2001 | Anderson et al. |
| 6,392,894 | B1 | 5/2002 | Buechler et al. |
| 6,394,952 | B1 | 5/2002 | Anderson et al. |
| 6,727,073 | B1 | 4/2004 | Moore et al. |
| 6,830,731 | B1 | 12/2004 | Buechler et al. |
| 6,867,051 | B1 | 3/2005 | Anderson et al. |
| 6,878,947 | B2 | 4/2005 | Haberstroh |
| 6,936,476 | B1 | 8/2005 | Anderson et al. |
| 7,002,688 | B2 | 2/2006 | Aravanis et al. |
| 7,437,913 | B2 | 10/2008 | Djennati et al. |
| 7,521,249 | B2 | 4/2009 | Rosen et al. |
| 7,521,260 | B2 | 4/2009 | Petruno et al. |
| D606,664 | S | 12/2009 | Jacono et al. |
| 7,632,687 | B2 | 12/2009 | Gokhan |
| 7,784,679 | B2 | 8/2010 | Kuo et al. |
| 7,925,445 | B2 | 4/2011 | Petrilla et al. |
| 8,039,783 | B2 | 10/2011 | Lai |
| 8,043,867 | B2 | 10/2011 | Petruno et al. |
| 8,128,871 | B2 | 3/2012 | Petruno et al. |
| 8,334,522 | B2 | 12/2012 | Egger |
| 9,207,181 | B2 | 12/2015 | Egan et al. |
| 2002/0190356 | A1 | 12/2002 | Buechler et al. |
| 2004/0018637 | A1 | 1/2004 | Polito et al. |
| 2004/0241047 | A1 | 12/2004 | Buechler et al. |
| 2005/0008538 | A1 | 1/2005 | Anderson et al. |
| 2005/0017076 | A1 | 1/2005 | Hosokawa et al. |
| 2006/0228554 | A1 | 10/2006 | Tan et al. |
| 2007/0154970 | A1 | 7/2007 | Buechler et al. |
| 2007/0236692 | A1 | 10/2007 | Schebesta et al. |
| 2008/0031779 | A1 | 2/2008 | Polito et al. |
| 2008/0081341 | A1 | 4/2008 | Maher et al. |
| 2008/0199851 | A1 | 8/2008 | Egan et al. |
| 2008/0311002 | A1 | 12/2008 | Kirby et al. |
| 2009/0061507 | A1 | 3/2009 | Ho |
| 2009/0090874 | A1* | 4/2009 | Roper .............. G01N 35/00029 250/484.4 |
| 2009/0142856 | A1 | 6/2009 | Hudak et al. |
| 2009/0263854 | A1 | 10/2009 | Jacono et al. |
| 2010/0068826 | A1 | 3/2010 | Gokhan |
| 2010/0117003 | A1 | 5/2010 | Egger |
| 2010/0135857 | A1 | 6/2010 | Hunter et al. |
| 2010/0311181 | A1 | 12/2010 | Abraham et al. |
| 2011/0043618 | A1 | 2/2011 | Salisbury et al. |
| 2012/0021531 | A1 | 1/2012 | Ellis et al. |
| 2012/0071342 | A1 | 3/2012 | Lochhead et al. |
| 2012/0223251 | A1 | 9/2012 | Morrow et al. |
| 2012/0300205 | A1 | 11/2012 | Misener et al. |
| 2013/0230844 | A1 | 9/2013 | Egan et al. |
| 2013/0230845 | A1 | 9/2013 | Egan et al. |
| 2016/0054316 | A1 | 2/2016 | Egan et al. |

FOREIGN PATENT DOCUMENTS

| | | | |
|---|---|---|---|
| EP | 0174722 | A2 | 3/1986 |
| JP | 2003-083970 | A | 3/2003 |
| WO | WO 1999/039298 | A1 | 8/1999 |
| WO | WO 2000/031539 | A1 | 6/2000 |
| WO | WO 2005/031355 | A1 | 4/2005 |
| WO | WO 2009/014787 | A2 | 1/2009 |
| WO | WO 2010081219 | * | 7/2010 |
| WO | WO 2013/131052 | A1 | 9/2013 |
| WO | WO 2013/131057 | A1 | 9/2013 |

OTHER PUBLICATIONS

Egan et al., "High sensitivity immunofluorescence influenza A+B assay with reader", 27th Annual Clinical Virology Symposium, May 8-11, 2011, 1 page (2011) Abstract.
Giebeler et al., "Performance validation for microplate fluorimeters", vol. 15, No. 3, pp. 363-375 (2005).
International Search Report from PCT Patent Application No. PCT/US2013/028743 dated May 28, 2013.
International Search Report from PCT Patent Application No. PCT/US2013/028749 dated Jul. 1, 2013, application now published as PCT Publication No. WO2013/131057 on Sep. 6, 2013.
International Search Report from PCT Patent Application No. PCT/US2014/068829 dated Mar. 6, 2015.
Van Dyke et al., "Multiplex point of care (POC) assay for the detection community acquired resoiratory viruses", 27th Annual Clinical Virology Symposium, Poster, May 8-11, 2011, 2 pages (2011) Abstract.

* cited by examiner

SYSTEM AND APPARATUS FOR POINT-OF-CARE DIAGNOSTICS

CROSS-REFERENCE TO RELATED APPLICATIONS

This application is a continuation of U.S. application Ser. No. 14/932,769, filed Nov. 4, 2015, now allowed, which is a continuation of U.S. application Ser. No. 13/783,019, filed Mar. 1, 2013, now U.S. Pat. No. 9,207,181, which claims the benefit of U.S. Provisional Application No. 61/666,689, filed Jun. 29, 2012; U.S. Provisional Application No. 61/636,105, filed Apr. 20, 2012; and U.S. Provisional Application No. 61/605,694, filed Mar. 1, 2012. Each of the aforementioned priority documents is incorporated herein by reference in its entirety.

TECHNICAL FIELD

The subject matter described herein relates to a system and an apparatus for analysis of a sample to aid in medical diagnosis or detection of the presence or absence of an analyte in the sample.

BACKGROUND

Diagnostic immunoassays are typically reliant on a color change or the production of color to reveal a result that is often visible by the human eye. As a result of the human perception and judgment involved, there is significant variance among those interpreting such test results as to whether a color change or other measurable signal has occurred, particularly if the signal is close to a threshold value. There can be, therefore, subjectivity involved in interpreting whether immunoassay results are positive or negative. Moreover, for detection of some analytes present in small quantities, a sufficient color change or color production is not possible for detection by the human eye. Accordingly, there remains a need in the art for an apparatus and a system that objectively analyses a signal from an immunoassay test device, to reduce the error associated with interpreting the result, and to improve the sensitivity of the device by providing an apparatus that can detect a small or weak signal imperceptible to the human eye.

BRIEF SUMMARY

The following aspects and embodiments thereof described and illustrated below are meant to be exemplary and illustrative, not limiting in scope.

In one aspect, an apparatus for detection of a signal from a test device indicative of the presence or absence of an analyte in a sample is provided.

In another aspect, a system comprising an apparatus and a lateral flow immunoassay test device is provided. The apparatus is comprised of a housing comprising a drawer movable between an open position and a closed position in which the drawer is contained within the housing; an optional bar code scanner positioned in the housing for reading an encoded label on a test assay to be inserted into the apparatus; a carriage movably mounted in the housing, the carriage comprising a source of excitation light and a photodetector for detecting energy emitted; drive electronics to move the carriage sequentially from a first position to a final position, and a plurality of positions there between, wherein the carriage has a dwell time at each of said plurality of positions between the first and final positions; and a processor for control of the drive electronics and carriage and for processing data detected by the photodetector.

The test device of the system is comprised of a test strip and an optional bar code label; a label pad on the test strip, the label pad comprised of microparticles comprised of a fluorescing lanthanide compound and an antibody with binding specificity of an analyte of interest; and a plurality of lines on the test strip, positioned downstream from the label pad, the plurality of lines comprising at least a reference line or a control line and an analyte-specific test line. Upon insertion of the test device into the drawer of the apparatus and moving the drawer into its closed position, (i) the bar code scanner, if present, obtains information from the bar code label on the test device housing, if present, regarding the analyte of interest to be detected. If the bar code scanner and/or bar code label is/are not present, the information is provided by a user, an external bar code scanner, or other mechanism. Then, based on the analyte of interest to be detected, the processor selects an analyte-specific measurement protocol wherein the carriage is moved from its first to final position, and at each position the photodetector detects light emitted from the test strip during an illumination period when the source of excitation light is on and during a dark period with the source of excitation light is not powered on. A one-dimensional data array is generated where the difference between light emitted in the illumination period and the light emitted in the dark period at each carriage position is generated by the processor, wherein data in the data array corresponding to the reference line or the control line is used to identify the location of data in the array that corresponds to the analyte-specific test line.

In one embodiment, the test device is a lateral flow immunoassay. In another embodiment, the test strip is in a housing member.

In one embodiment, the drawer comprises at least one arm for positioning the test device (e.g., lateral flow immunoassay) in a predefined position for interaction with the movable carriage.

In another embodiment, the source of excitation light is a light emitting diode. For example, the light emitting diode can emits light at about 365 nm. In another embodiment, the light emitting diode is provided with at least about 4 mW.

In yet another embodiment, the apparatus further comprises a socket for insertion of a memory device. In one embodiment, the memory device has a read only capability or a read-write capability.

In yet another embodiment, the apparatus further comprises a port for connection with an external instrument. In still another embodiment, the external instrument is selected from a computer, a storage device, a bar code scanner, and a laboratory instrument.

In one embodiment, an internal bar code scanner is present in the apparatus, and the internal bar code scanner is comprised of a light source, a lens and a light sensor that translates optical impulses into electrical impulses, and wherein one or more mirrors are positioned to achieve interaction of light from the bar code scanner light source and a bar code label on a test device inserted into the apparatus.

In still another embodiment, the plurality of lines on the test device is comprised of, in an upstream to downstream direction with respect to flow of fluid on the test device, a negative control line, an analyte-specific test one, and a reference line. In one embodiment, the reference line comprises antibodies for non-specific binding to immunoglobulins present in a sample, and based on its fluorescent signal communicates to the processor whether sufficient sample has reached the reference line and provides a positional reference for determining the position of the analyte-specific test line.

In yet another embodiment, the reference line is dimensionally wider than the analyte-specific test line.

In one embodiment, a first derivative of the data array is calculated, and a minimum peak and a maximum peak corresponding to the reference line is used to determine a cutoff value for analysis of data corresponding to the analyte specific test line.

In another embodiment, the plurality of lines includes a negative control line comprised of antibodies with non-specific binding to immunoglobulins in a sample.

In another embodiment, a first derivative of the data array is calculated, and a minimum peak and a maximum peak corresponding to the negative control line is used to determine a cutoff value for analysis of data corresponding to the analyte specific test line.

In still another embodiment, the fluorescing lanthanide compound is europium. In one embodiment, the microparticles are comprised of a europium core with a polystyrene exterior.

In yet another embodiment, a splash shield is positioned between the immunoassay test device and the carriage to protect the photodetector and/or source of excitation light from sample on the immunoassay test device.

In still another embodiment, a sample placed on the test device flows in an upstream to a downstream direction, from a sample pad downstream to the region comprising a plurality of line, and wherein the movable carriage scans the test device in a downstream to upstream direction.

In another aspect, a kit, comprising a system as described herein and a calibration cassette comprised of at least two lines that fluoresce upon excitation with the light source is provided.

In one embodiment, the at least two lines that fluoresce are comprised of a fluorescing compound deposited on a biaxially-oriented polyester.

In another embodiment, the kit additionally comprises a memory device, such as an SD card, with information encoded or stored thereon.

In another aspect, a method for detecting the presence or absence of an analyte in a sample is provided. The method comprises applying a sample to a test device (also referred to generally as a test strip), exemplified by a lateral flow immunoassay, that comprises a plurality of lines comprised of a control line or a reference line and an analyte-specific test line, wherein each of the line in the plurality comprise a label that fluoresces or luminesces upon illumination, and the analyte-specific test line comprises an antibody specific for an analyte of interest in the sample, the antibody associated with the detectable label; inserting the test device into a receiving member in an apparatus comprising a movable optics module, the optic module comprised of an illumination source and a photodetector; moving the optics module incrementally in a downstream to upstream direction with respect to fluid flow on the test device, where the optics module pauses for a dwell time at each incremental position, and at each position the illumination source is turned on and then turned off, and the photodetector detects a signal (e.g., light) emitted by the test device when the illumination source is on and when the illumination source is off; and processing the emitted light data by generating a one-dimensional data array of the difference in emitted light when the illumination source is on and when the illumination source is off at each incremental position, and calculating a first derivative of the one-dimensional array to generate a derivative data set, wherein the first maximum peak in the derivative data set corresponds to data from the reference line or the control line, and is used to identify the location of data in the derivative data set for the analyte-specific test line.

In one embodiment, the analyte of interest is an infectious analyte. Exemplary infectious analytes include a virus or a bacteria, such as influenza A or influenza B.

In another embodiment, the test device comprises an analyte-specific test line for influenza A and an analyte-specific test line for influenza B.

In another aspect, an apparatus comprising the following elements is provided: a housing comprising a drawer movable between an open position and a closed position where the drawer is contained within the housing; an optional bar code scanner positioned in the housing for reading an encoded label on a test assay (or test device) to be inserted into the apparatus; a carriage movably mounted in the housing, said carriage comprising a source of excitation light and a photodetector for detecting energy emitted; drive electronics to move the carriage sequentially from a first position to a final position, and a plurality of positions there between, wherein the carriage has a dwell time at each of said plurality of positions between the first and final positions; a processor for control of the apparatus, wherein the processor comprises a software program that processes data obtained from the photodetector by generating a data array comprised of emitted signal at each incremental position between the first and final positions, taking the first derivative of the data array to form a derivative data set, wherein a first maximal value in the derivative data set corresponds to a maximum signal from a reference line or a control line on the test device, and the position in the derivate data array of the first maximal value determines the position of data from the analyte-specific test line.

In addition to the exemplary aspects and embodiments described above, further aspects and embodiments will become apparent by reference to the drawings and by study of the following descriptions.

Additional embodiments of the present systems, apparatus and methods will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the system, apparatus or method. Additional aspects and advantages of the present systems and apparatus are set forth in the following description and claims, particularly when considered in conjunction with the accompanying examples and drawings.

DETAILED DESCRIPTION

I. Definitions

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Where a range of values is provided, it is intended that each intervening value between the upper and lower limit of that range and any other stated or intervening value in that stated range is encompassed within the disclosure. For example, if a range of 1 µm to 8 µm is stated, it is intended that 2 µm, 3 µm, 4 µm, 5 µm, 6 µm, and 7 µm are also explicitly disclosed, as well as the range of values greater than or equal to 1 µm and the range of values less than or equal to 8 µm.

As used in this specification, the singular forms "a," "an," and "the" include plural referents unless the context clearly dictates otherwise. Thus, for example, reference to an "antibody" includes a single antibody as well as two or more of the same or different antibodies, reference to an "excipient" includes a single excipient as well as two or more of the same or different excipients, and the like.

II. System

In one aspect, a system comprised of a test device and an apparatus capable of optically detecting a signal is provided. The test device and the apparatus are designed for unique interaction with each other, as will now be described. In the description below, the test device is exemplified by a lateral flow immunoassay, and is sometimes referred to as a test strip. It will be appreciated that the test device is not intended to be limited to the lateral flow immunoassay test device used to exemplify the system, and a skilled artisan will appreciate that other test devices, such as microfluidic devices, immunoassays other than lateral flow based immunoassays, are contemplated.

A. Apparatus

Figure 1A:
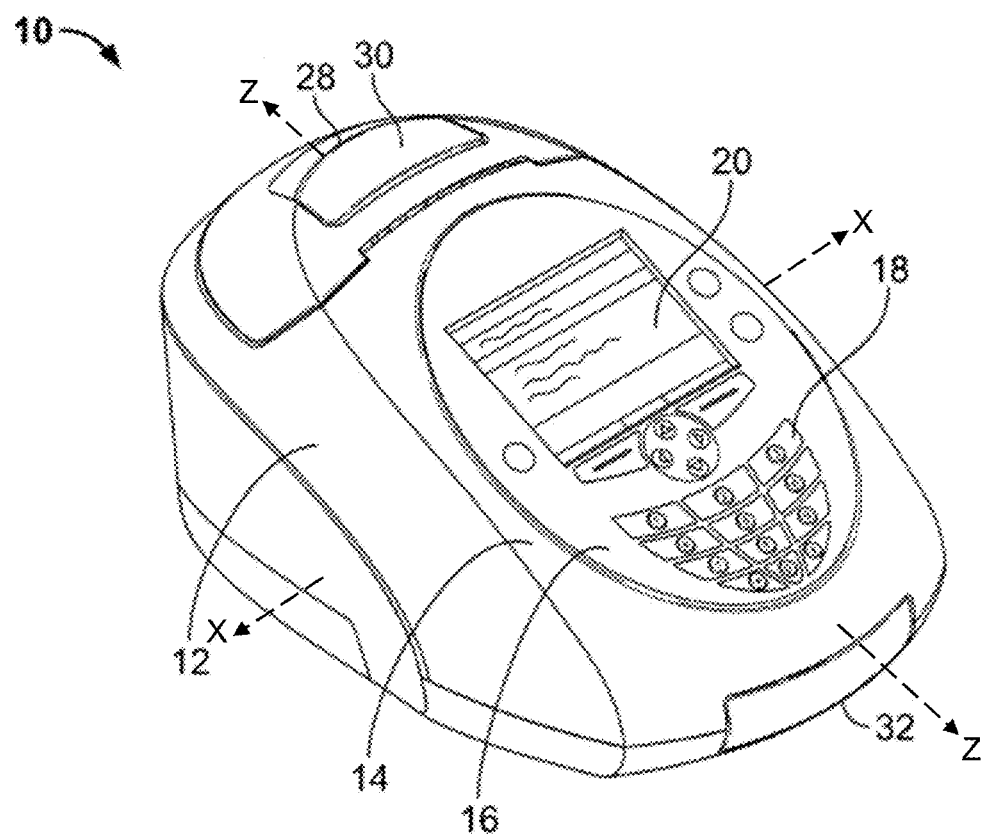
FIGS. 1A-1B are front perspective (FIG. 1A) and a back view (FIG. 1B) of an exemplary apparatus.
Figure 1B:
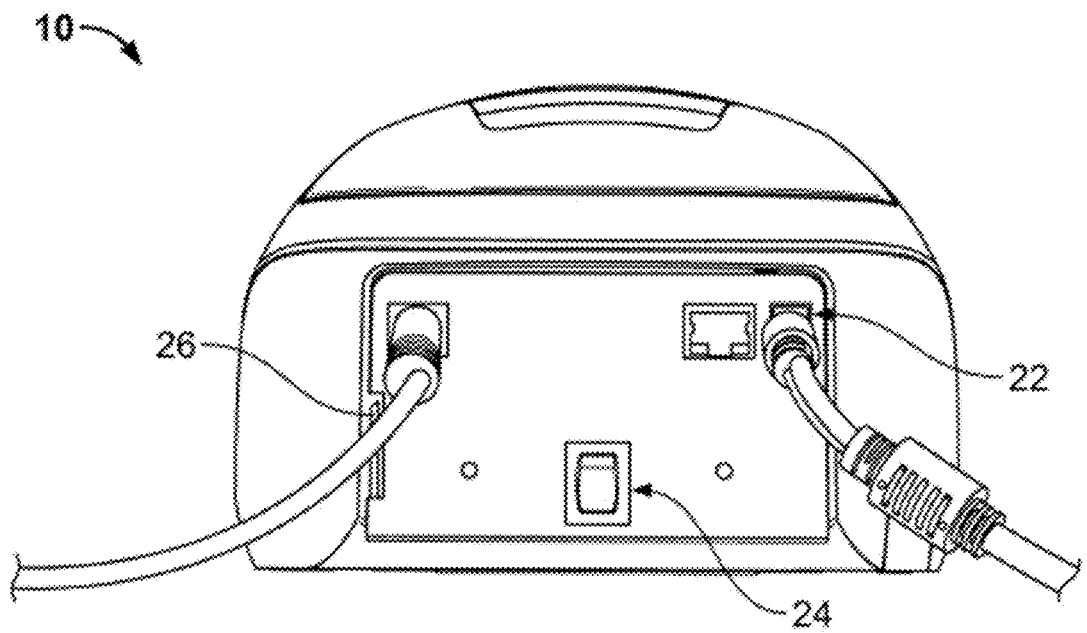

An embodiment of an apparatus capable of detecting a signal produced by a test device is illustrated in FIGS. 1A-1B. Apparatus 10 includes a housing 12 that encloses an optics system, electronics software, and other components of the apparatus, all to be described herein below. A front side 14 of the apparatus includes a user interface 16 that may include, for example, a key pad 18 and a display screen 20. The key pad includes numeric keys for entry of numeric values, which can also be labeled with letters of the alphabet, a decimal point key, a back space key, and other keys that are desired by end users. As part of the key pad or as separate keys positioned elsewhere on the apparatus, the device may include keys to print test results, to advance printer paper, to open or close a drawer in the device, directional arrow keys and soft or select keys for a user to interact and instruct the apparatus. In one embodiment, the key pad is an alpha/numeric key pad, and the apparatus includes a print key to activate print feature of a test result; a paper advance key; navigation screen keys for a user to navigate through menu options displayed on interface screen (for example, right/left/up/down keys, select keys).

The display screen can be, for example, a liquid crystal display screen, to receive output from a data processing unit in the apparatus and display it to a user of the apparatus. In one embodiment, the display screen is a touch screen, for interaction with a user. An exemplary screen is a color screen with resolution of 320×240 (1/4 VGA) and adjustable contrast and brightness. Visible on the screen to a user will be information such as test results, error messages, instructions, calibration information, troubleshooting information, user information, and the like.

An embodiment of the rear panel of apparatus 10 is shown in FIG. 1B and can include port to receive a source of AC power 22 and an on/off toggle switch 24, which in this embodiment is a soft key to activate the software. The apparatus may additionally provide ports, on the rear panel or elsewhere on the apparatus, to connect optional components and/or to interface with external instruments. For example, the apparatus may include a PS2 connector, for example, to interface with an external barcode reader; a port, such as an RJ45 port, to connect to a local area network or Ethernet; a removable memory card port or slot; and/or a USB port. In a preferred embodiment, the apparatus includes a slot or port 26 for insertion of a removable non-volatile flash memory card, such as an SD card, and the apparatus is capable of read and write operations to and from the SD card, to, for example, store all scan data from each test device, update system software.

With reference again to FIG. 1A, the apparatus can also include a printer, such as a thermal printer, resident within the housing, and an opening 28 in a removable cover 30 on the housing is provided through which paper from the internal printer exits the housing. The removable cover provides access to access or replenish a paper supply (not visible in FIG. 1A) that interacts with the printer inside the apparatus.

Figure 2A:
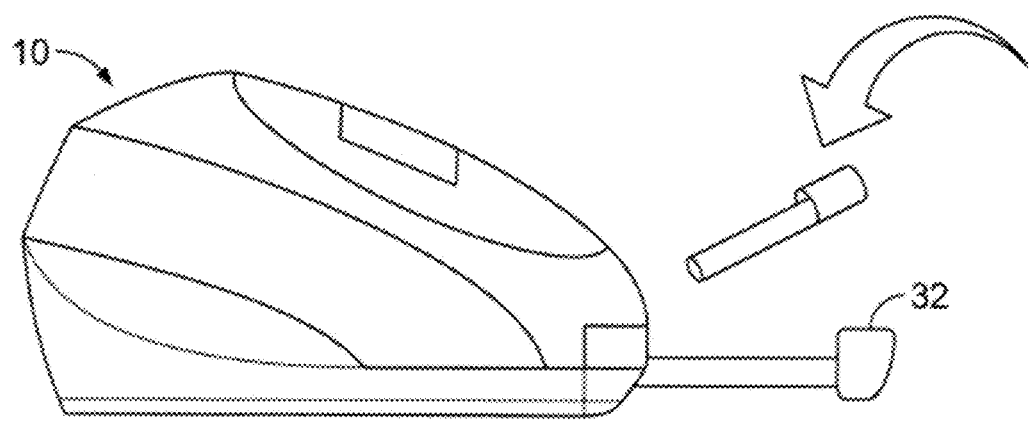
FIGS. 2A-2B are views of an exemplary apparatus showing a side view of the apparatus with the drawer in an open position (FIG. 2A) and a top perspective view of the drawer in an open position with a lateral flow immunoassay test device inserted into the drawer (FIG. 2B)
Figure 2B:
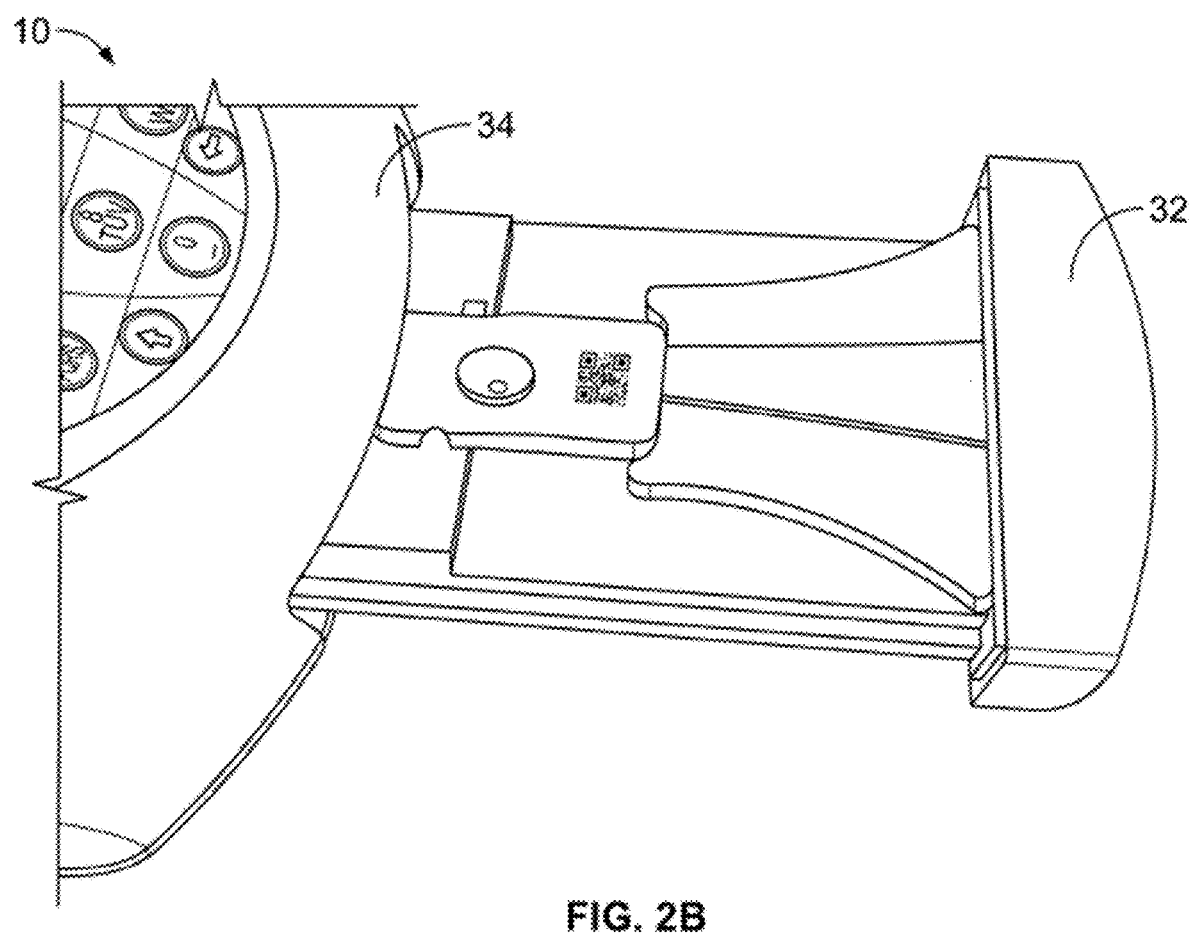

The apparatus also includes a drawer 32 movable between open and closed positions, as shown in FIG. 1A in its closed position and in FIGS. 2A-2B in its open position. In the embodiment shown, the drawer is positioned on a front edge 34 of the apparatus, as seen best in FIG. 2B. It will be appreciated that the drawer could also be positioned on either side of the apparatus. In one embodiment, the drawer moves between its open and closed positions by a mechanical mechanism, such as a latch and spring mechanism. In one embodiment, the draw opens in response to a user activating a key on the front or face of the apparatus, such as an "open drawer" or "eject test device" button. In one embodiment, the drawer is moved into its closed position after insertion of a test device manually by a user, or in response to a user activating a key or button on the apparatus. The drawer is configured to receive an immunoassay test device, further described below. Within the drawer, in one embodiment, is a distinct region, for example a depression, sized to receive the test device. During operation of the apparatus, the test device remains in a stationary position in the drawer, and therefore is positioned with precision in the apparatus for precise interaction with a movable optics system, described below. Accordingly, the drawer comprises in one embodiment a mechanism for positioning the test device for interaction with the optics system. An exemplary embodiment of a positioning mechanism is illustrated in FIGS. 3A-3B.

Figure 3A:
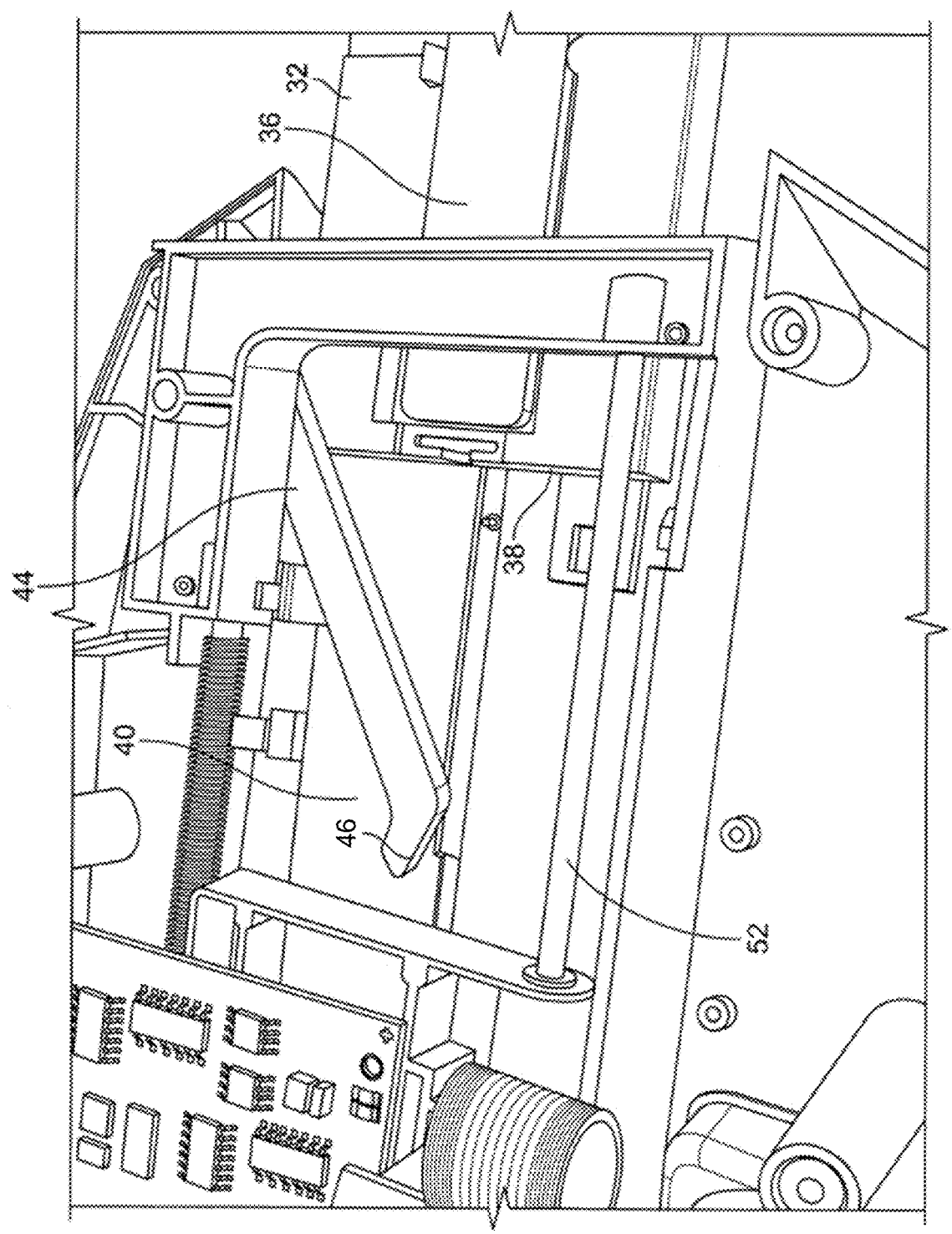
FIGS. 3A-3B are close-up views of the drawer in the apparatus in an open position (FIG. 3A) and in a closed position (FIG. 3B), with a test device positioned in the drawer.

FIG. 3A is an illustration of the internal components in the area of the drawer in the apparatus, which are visible to a user only upon removal of the housing. In FIG. 3A, drawer 32 is in its open position, and a test device 36 is positioned in the drawer for insertion into the apparatus. A distal edge 38 of drawer 32 remains inserted within the apparatus when the drawer is in its open position, with a proximal edge of the drawer being the portion of the drawer closest to a user and that enters and exists the apparatus during use. Within the apparatus is a receptacle 40 into which drawer 32 can be received when the drawer is moved into its closed position. Extending into receptacle 40 is a positioning arm 42 with a first end 44 and a second free end 46. First end 44 is movable within a track or slot 48 in the receptacle. The arm is dimensioned and positioned such that its free end 46, or at least a corner of the free end, of the arm contacts an edge of the test device 36 when the drawer is moving between its open and closed positions. This is apparent from the view shown in FIG. 3B, where the drawer is in its closed position and a corner of the free end of the arm is in contact with the test device, and specifically with an edge of the test device exemplified by an optional housing surrounding a lateral flow immunoassay. The arm via its contact with the test device gently presses the test device to a specific position within the drawer, and more specifically within the slot in the drawer that is dimensioned to receive and hold the test device.

Arm 42 is dimensioned and positioned to ensure precise lateral positioning of the test device in the apparatus, more specifically, precise positioning in a plane that passes through the apparatus in a side to side direction with respect to the left/right sides of the apparatus. This plane is denoted by the x-x arrows in FIG. 1A. A second arm can also be provided, to precisely position the test device along an axis running from the front to back of the apparatus, referred to as a longitudinal axis and denoted by the z-z arrows in FIG. 1A. In one embodiment, a second arm is located at a proximal end 50 of the drawer, to press against the test device to position it in the horizontal plane. The second arm, in one embodiment, is under tension by a spring, and in other embodiments is movable laterally and positioned to have a pressure point when in contact with a frontal edge of the test device.

Figure 3B:
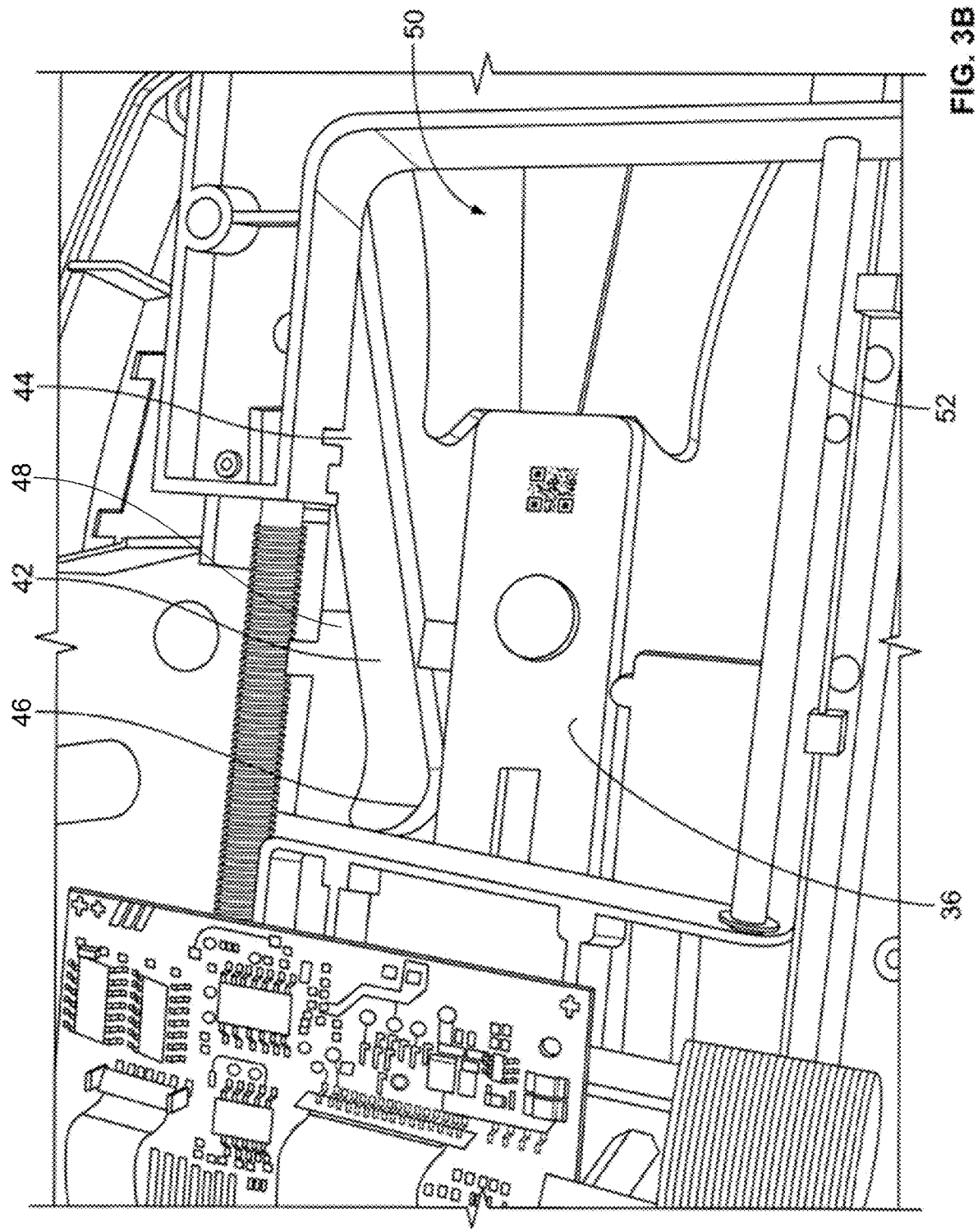
Figure 4:
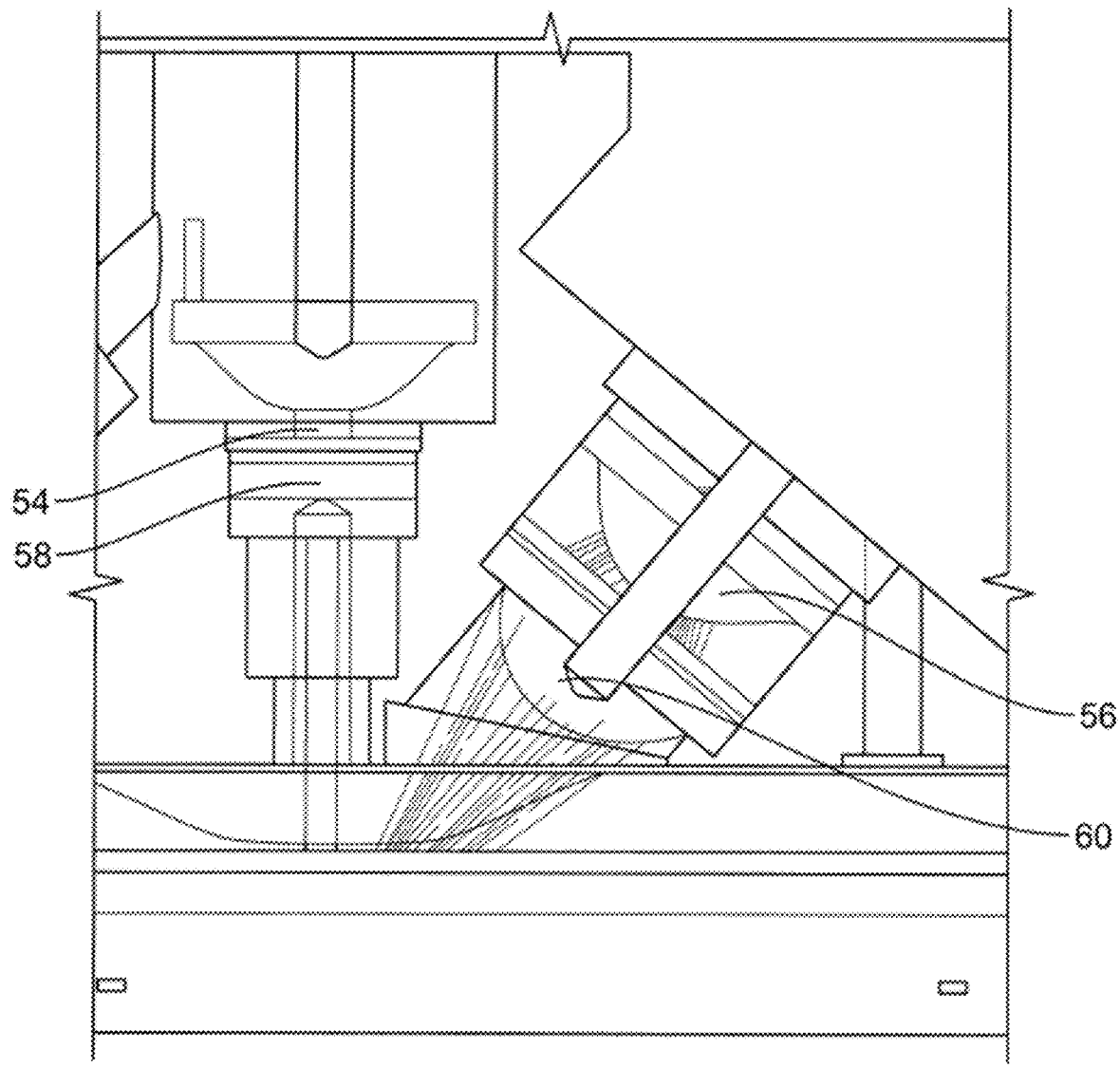
FIG. 4 is a schematic of the optics system within the apparatus.

Visible in FIGS. 3A-3B is a support rod 52 that extends at least the length of receptacle 40. Support rod 52 provides a track along which a movable optics system in the apparatus travels, to scan the stationary test device inserted into the apparatus. The optics system is now described with reference to FIG. 4.

A microprocessor-controlled optics system is positioned within the housing of the apparatus such that it moves along the longitudinal axis (denoted by the z-z arrows in FIG. 1A) from a home or start position to a final position. The optics system includes an optics module comprised of a carriage mounted on a track, the carriage movable by an electric motor or actuator within the optics system of the apparatus. Secured to the carriage, and part of the movable optics module, are an illumination source 54 and a detector 56, such as a photodiode. The illumination source can be mounted perpendicular to the test device and the detector is oriented at an angle to collect emission from the test device. In the embodiment shown in FIG. 4, a photodiode is oriented at 40° relative to the test device, and more generally the detector can be oriented at an angle of between about 20°-75° relative to the surface of the test device. In one embodiment, the optics module includes a single element optical detector (that is, an array of optical detectors is not present) and a single illumination source. The optics module can also comprise one or more filters, and the embodiment illustrated includes a filter 58, and preferably a long pass filter, on the emission side of the illumination source, and a filter 60 positioned between the test device and the detector. In one embodiment, the illumination source emits UV light at a wavelength that matches the excitation wavelength of a label in the test device. In one embodiment, the illumination source is a light emitting diode (LED) that has a peak emission at 365 nm, more generally of between about 320-390 nm or 325-380 nm. In this embodiment, the long pass filter positioned in the optical path from the LED to the test device transmits light between 310-315 nm.

In one embodiment, the photodetector is a broad band detector suitable to detect light at the wavelength emitted from the label in the test device. In one embodiment, the photodetector is a single-element photodetector (i.e., is not an array of photodetectors). In one embodiment, the label is or contains a fluorescent, luminescent, chemiluminescent compound. As will be described below, an exemplary fluorescent label is a lanthanide ion, such as europium, samarium, terbium and holmium, which each fluoresce at specific wavelengths. Filter 60 positioned in the optical path between the test device and the detector, in one embodiment, transmits light above about 515 nm for detection by the detector. A skilled artisan will appreciate that a variety of filters are known in the art (longpass, shortpass, bandpass, etc.) and can be selected according to the wavelengths of light desired to excite a label and the wavelength of light desired for detection.

The optical system can also include an optical feedback loop. The intensity or light output of the illumination source is controlled by a feedback loop using a monitor diode in the illumination path of the optics. Power to the illumination source is adjusted based on light output, where if, for example, light output decreases, current is increased to compensate. In one embodiment, the power output from the illumination source is between 2-5 mW, more preferably between 2.5-5 mW. The feedback loop subsystem ensures consistent light output from the illumination source and reduces the frequency that calibration of the optical system in the apparatus is required.

Resolution of the optics system to resolve or discriminate individual, discrete lines on the test device is a feature of the optics system, as will become apparent from the description of the test device and operation of the apparatus below. The illumination source preferably provides a focused beam of light capable of resolving one or more lines on a test device that are between 1-1.2 mm apart, or 4 mm apart measured from the center of a first line and the center of an adjacent line. In one embodiment, the shape of the beam of light from the illumination source is 2.5 mm by 0.8 mm, more generally is between 2-3 mm by 0.5-1.2 mm. In another embodiment, the illumination source illuminates localized regions of the detection zone on a test device (described below) and the single-element detector is synchronized with the illumination source in incremental movement along a movement path, thus permitting synchronized illumination in a localized region and detection in the localized region. A field stop is provided to determine the shape of the beam of light, and can be tailored according to the spacing between and width of the test lines on the test device. As will be described below, in one embodiment, the spacing or tolerance between two adjacent test lines on the test device and the shape of the beam of light are selected to provide a dark space between test lines where no emissivity signal occurs.

In one embodiment, the optical system comprises a splash shield positioned between the sample input on the test device and the optical system, to protect the optics system and its movable module from liquid sample that may linger in the sample port/sample pad, particularly when the device is operated in walk-away mode, described below.

The apparatus, in some embodiments, includes a temperature sensing means, and in a preferred embodiment, includes at least two temperature sensing devices housed within the housing of the apparatus. A first internal temperature sensor is positioned to detect the temperature in the region associated with the optics system and a second internal temperature sensor is positioned elsewhere in the apparatus away from any internally generated heat source in order to detect ambient temperature of the environment in which the apparatus is operated.

The apparatus includes internal memory storage with necessary software for operation and for storage of data collected from sample analysis. By the SIM port or by an external computer (wireless or wired attachment), data can be exported from the apparatus or imported to the apparatus.

Figure 5:
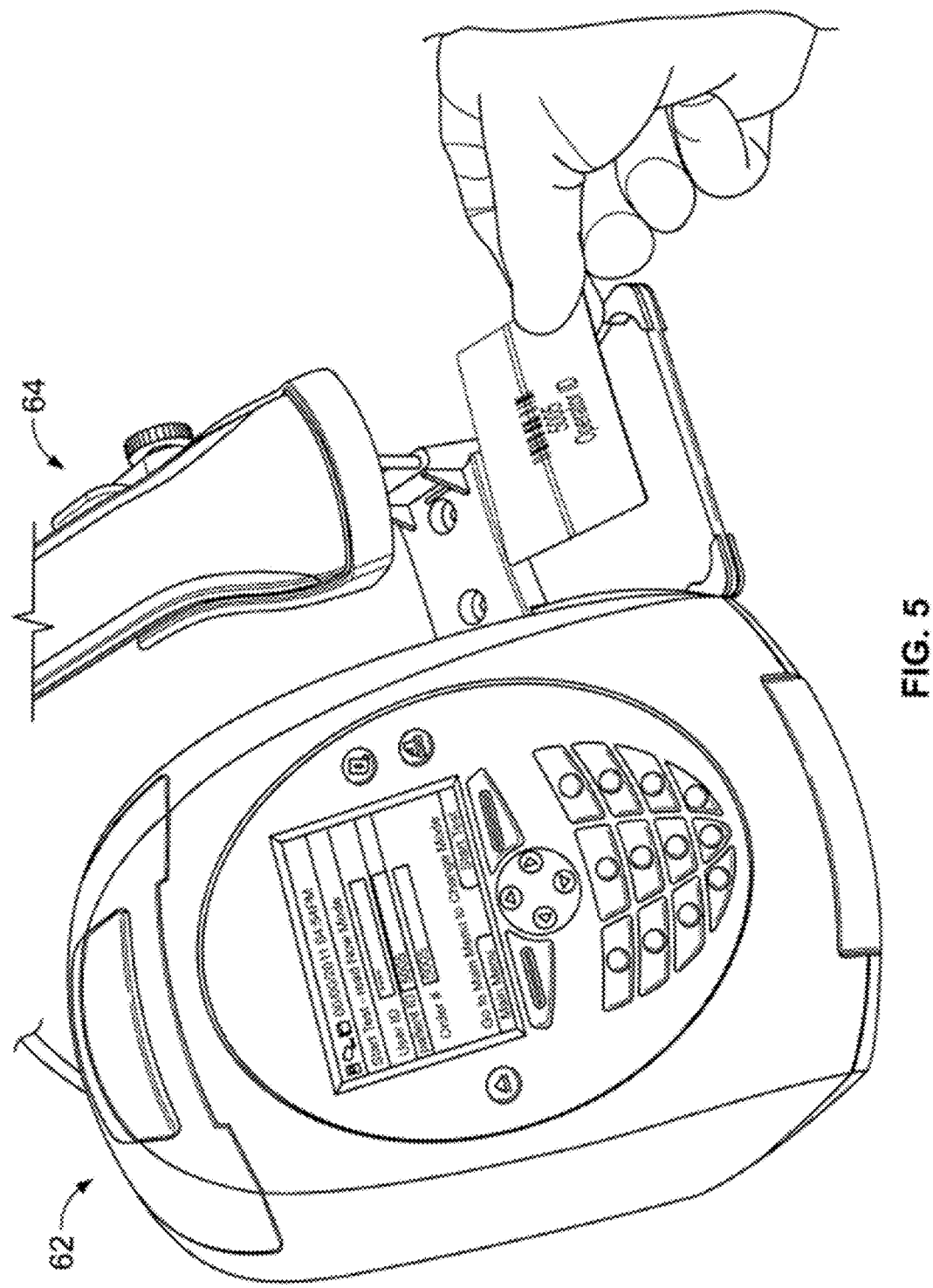
FIG. 5 is a view of an exemplary apparatus with an optional bar code scanner device attached.

As mentioned above with reference to FIG. 1B, the apparatus is equipped with ports for attachment to optional external devices, and an example is illustrated in FIG. 5. In this embodiment, the front or user side of an apparatus 62 is shown, and attached to the apparatus is an external bar code scanner 64. The bar code scanner interfaces with the apparatus via a suitable data port provided on the apparatus. Externally attached devices ease transfer of data into and from the apparatus, and can eliminate user keyboard input, permitting accurate data input into the apparatus regarding a test to be analyzed or patient or sample information. In one embodiment, a barcode scanner external is attachable via PS-2 port on the apparatus and is capable of reading a linear or 1D bar code.

In one embodiment, the apparatus is wireless or wired connected to a device for delivering medical data to a third party such as the Centers for Disease Control (CDC). In an exemplary embodiment, the apparatus communicates wirelessly with the 2Net™ Platform available from Qualcomm Life. The 2Net™ Platform is a cloud-based system that allows for the secure transfer of data from the apparatus for storage. The 2Net™ Platform gateways include, but are not limited to, a 2Net™ Hub, a stand-alone FDA-listed external device, and a cellular component embedded in the apparatus. Data from the apparatus is transferred to a cloud via a 2Net™ Platform gateway where it can be stored, manipulated, and/or shared. In an exemplary embodiment, the data may be transferred to the CDC for reporting and/or surveillance of infectious agents. In this embodiment, it is preferable that the date be manipulated, such as "de-identified", after transmission to the cloud storage to comply with applicable rules and regulations such as HIPAA. It will be appreciated that the data may be transferred to one or more cloud storage sites (e.g. from a third-party cloud such as Qualcomm to a proprietary cloud). In one specific non-limiting embodiment, data from the apparatus is wirelessly transmitted to a Qualcomm cloud via the 2Net™ Hub. The data is then transferred to a proprietary cloud where it is "de-identified" to remove user information for compliance with HIPAA rules and regulations. The data is then transferred to the CDC for surveillance of infectious agents.

The apparatus can include additional optional features, including for example acoustical output capability, to generate tones for audible feedback to a user, such as an error or test completion.

Calibration Cassette for Optics System

As described above, the apparatus comprises an optics system comprised of an optics module that includes a light source, which in one embodiment is an LED light source with a peak emission at 365 nm. The detector for the emitted fluorescent light from a label in a test device is a photodiode with filters to ensure that the light from the fluorescent reagent is not contaminated by ambient nor excitation light. Signal from the photodiode is translated through an analog to a digital converter where the digital signal is processed by a microprocessor in the apparatus into a test result. To ensure consistent light output, the LED has a feedback loop whereby the optics system monitors the light output of the LED and triggers an adjustment of the electrical current to the LED to ensure a consistent intensity of the excitation light beam in real time. To further ensure that signal drift is controlled, the apparatus has a calibration algorithm that enables the user to insert a calibration cassette specifically designed for the apparatus and provided with the apparatus. The calibration cassette is illustrated in FIG. 6.

Figure 6:
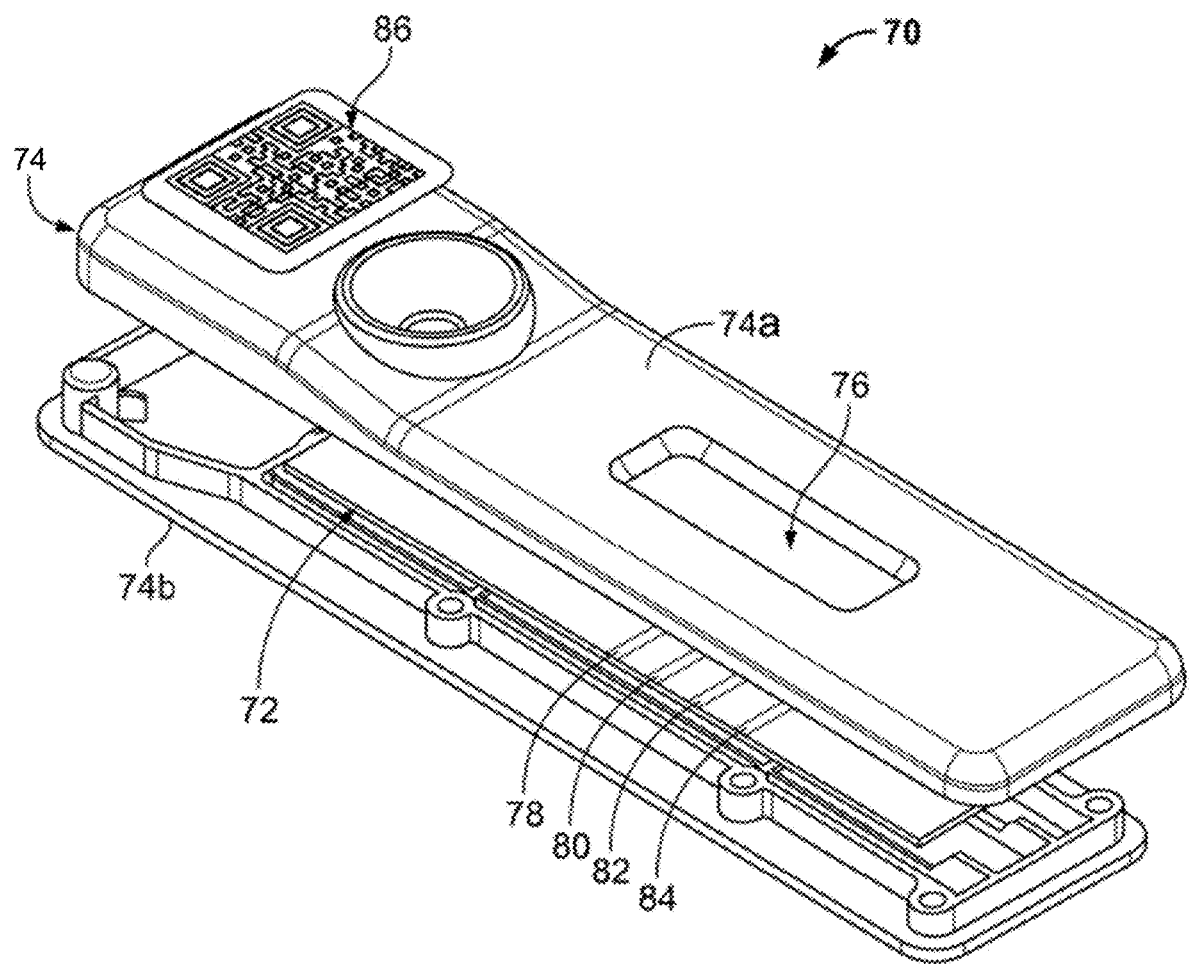
FIG. 6 is a view of a calibration cassette.

FIG. 6 shows a calibration cassette 70 comprised of a calibration strip 72 secured within an optional housing member, such as housing member 74 which is separable in this embodiment into upper member 74a and lower member 74b. A window 76 in upper housing member 74a is provided so that the optics system in the apparatus can interact with one or more lines on the calibration strip.

The calibration strip can comprise one or more lines, and in various embodiments, comprises two or more lines, three or more lines or four or more lines. In another embodiment, the calibration strip comprises at least two lines, at least three lines, or at least four lines. The embodiment illustrated in FIG. 6 shows a calibration strip with four lines, identified as 78, 80, 82 and 84, and referred to herein below as calibration lines or calibration test lines. The calibration lines are positioned on the strip relative to the housing to be visible through the window when the strip is secured within the housing. In one embodiment, the calibration strip is comprised of a material that fluoresces upon excitation by light from the illumination source in the optics system of the apparatus at a wavelength detectable by the photodiode subsequent to passage through any filter(s) in the light path of the photodiode. In one embodiment, the calibration strip is comprised of a material that fluoresces, and the calibration lines are defined by masking. For example, the fluorescing material can be silk-screened with a material that blocks light leaving the one or more calibration lines exposed. Alternatively, a fluorescing material can be deposited in discrete lines onto a non-fluorescing material. In one embodiment, the fluorescing material in the calibration strip is a fluorescent whitening agent deposited on or dispersed in a support material. Exemplary fluorescent whitening agents optical brightener are dyes that absorb light in generally the ultraviolet and violet range (340-370 nm) of the electromagnetic spectrum and re-emit light in the blue region (typically 420-470 nm). Exemplary optical brighteners include compounds such as stilbenes (di-, tetra-, or hexa-sulfonated), coumarins, imidazolines, diazoles, triazoles, benzoxazolines, biphenyl-stilbenes. A specific exemplary class of compounds are thiophenediyl benzoxazole compounds, and a specific exemplary fluorescent whitening agent is 2,5-thiophenediylbis(5-tert-butyl-1,3-benzoxazole), an optical brightener. Exemplary support materials include polymers, and particularly plastics, such as polymethylmethacrylates and polyesters, in particular biaxially oriented polyester. The whitening agent can be polymerized with the support material during manufacture of the polymeric support material, or can be deposited onto the polymeric support after its manufacture. In a preferred embodiment, the fluorescing material forming the one or more calibration lines on the calibration cassette fluoresces between 500-550 nm when excited.

The calibration cassette can optionally include a label, such as bar code 86 on the cassette in FIG. 6. In one embodiment, the bar code is a two-dimensional bar code with information, for example, to confirm for the apparatus that the cassette is a calibration cassette and with information regarding an expiration date for the cassette.

The calibration cassette is dimensioned to fit within the drawer of the apparatus, for interaction with the optics system, and in one embodiment the apparatus and a dedicated, specific calibration cassette are provided together as a kit. A user of the apparatus, typically when prompted by the apparatus at a regular, defined period, such as every 30 days, or once a month, or once every two months, etc., inserts the calibration cassette into the drawer of the apparatus. The internal bar code reader within the apparatus transfers the information on the barcode of the calibration cassette to the processor in the analyzer. It will be appreciated that the internal bar code reader is an optional feature, as the information on the bar code label can be entered into the apparatus by a user using the key pad or via an external bar code scanner. From this information, the analyzer will confirm that a calibration cassette has been inserted into the analyzer, provide target signals the analyzer uses for comparison to actual signals obtained for the calibration lines on the calibration strip, and provide the expiration date of the calibration cassette. The analyzer then activates the optics system to initiate illumination of the calibration cassette, and specifically sequential illumination of each of the calibration lines visible within the calibration cassette window. The analyzer then detects the fluorescent signal from each of the calibration lines and stores the signal in memory. The detected signal for two of the calibration lines is compared to the target (expected) signal for that calibration line. If the detected signal for each of two of the calibration lines is within a predefined range of the target signal, for example within (+/−) 1.75, 2%, 2.25%, 2.5% or 3%, then the calibration of the analyzer is valid and no adjustments to the apparatus are needed. This calibration check event is recorded and stored in the memory of the apparatus.

If the detected signal for either or both of two of the calibration lines is outside the predefined range of the target signal, but not outside of a maximum predefined range, for example outside+/−3.25%, +/−3.5%, +1-3.75% or +/−4% of a predefined target signal for a specific line, the processor in the analyzer activates an algorithm to self-calibrate using a third or different calibration line on the calibration test strip. Information for the target (expected) signal from this third line is also in the barcode information and was conveyed to the apparatus upon insertion of the calibration cassette and scanning of the bar code. When the signal for this third calibration line is within a defined acceptable range, the analyzer again reads the first two calibration lines to confirm that the expected target signal is detected for these two lines. If the signal is outside the maximum range, the analyzer cannot recalibrate itself, and the system generates an error message that is displayed to the user.

Apparatus Software

The apparatus includes an integrated software system used to collect data from the lateral flow test assay, process the data, and display a result to the user. The software can vary according to, for example, the design of the lateral flow test assay. An exemplary test assay is described below along with software tailored to control the apparatus' interaction with the exemplary test assay. Here, a general description of the software requirements is provided.

The software requirements are based on the test strip features and requirements. These include the functional and non-functional requirements the software desirably meets in order to fulfill assay requirements and user needs. The software specifications preferably include three modes of user operation: Operator, Supervisor, and Service. In addition to the main user modes, the software specifications preferably include ethernet/Laboratory Information System (LIS) communication, printing, SD card interface and barcode scanner functionality. The software specifications preferably also provide power on/off processing, battery, error handling, languages and audio notification. The software specifications preferably comprise the following high level functions: analyzing fluorescent data from a test device, a calibration cassette, or a quality control test; self calibration; managing users for login; storing, managing, and recalling test results; managing internal settings; printing results; sending results to a LIS; installing and operating in languages other than English; internal software checks, either at startup or continuously. In one embodiment, the software specifications preferably check all or some of the following, either at startup or continuously: memory, power supply; optics performance; stepper motor functionality; internal temperature; internal clocks; and barcode reading. If errors occur, they are logged in a message log and if applicable, the user is informed. The apparatus is designed to recover from errors in a safe manner.

Figure 7:
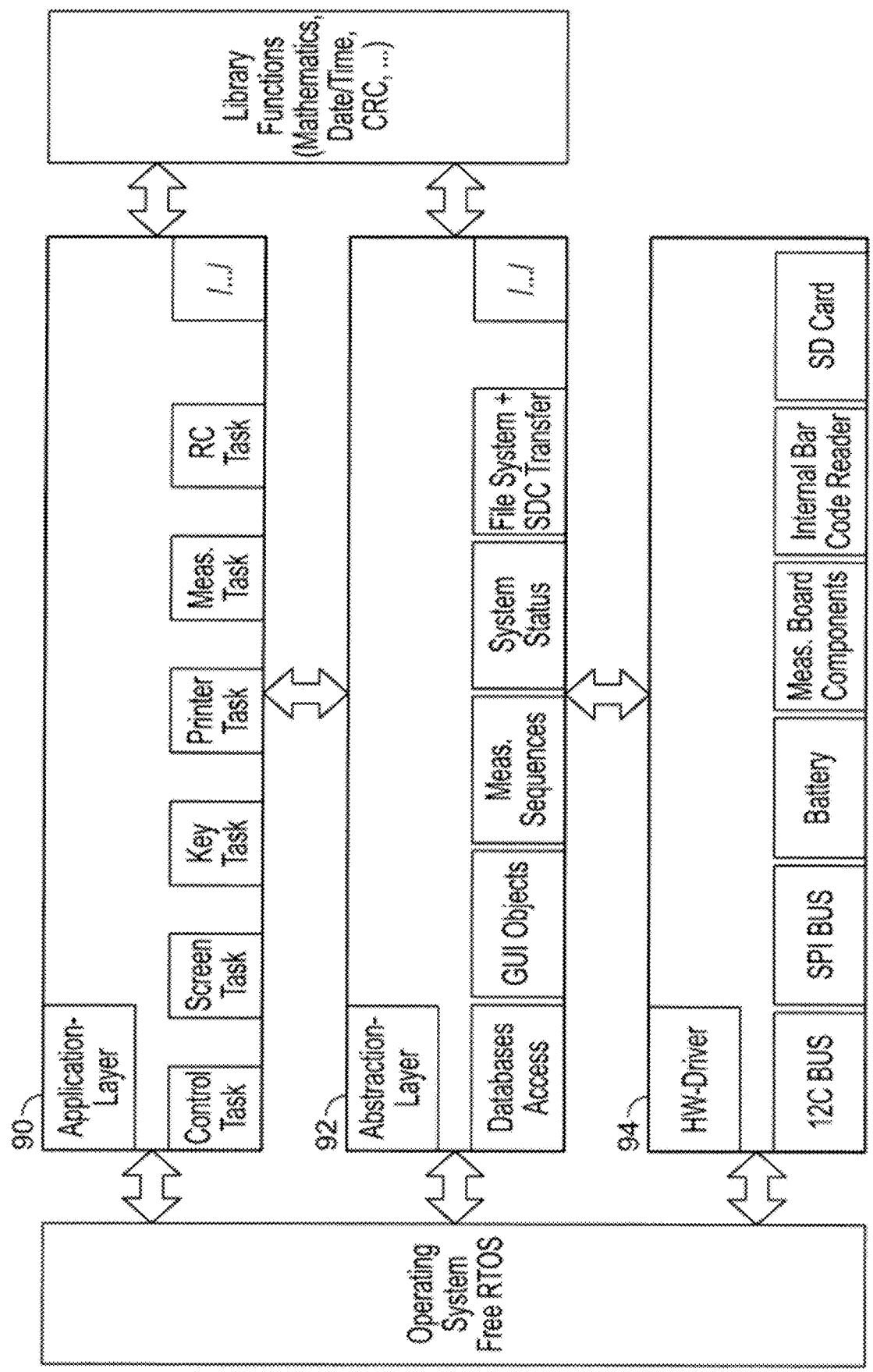
FIG. 7 is an illustration of the software architecture of an apparatus.

The apparatus software is based on 3-tier architecture, illustrated in FIG. 7. In brief, the software includes an application layer 90 that functions to controls the system tasks. These are separate tasks that run in parallel and perform dedicated functions. This includes, for example, controlling measurement scans, updating the graphical user interface (GUI) screens, accepting keypad user input, printing and performing remote communications. The tasks interact via message queues. A scheduler looks for tasks ready to run and activates them. The software also includes an abstraction layer 92 comprised of module groups that build up separate software subsystems. This builds a "convenience layer" for the application layer. The software subsystems include the data base subsystem, GUI objects, measured sequences, system status and SDC transfer. The software also includes a hardware (HW)-driver level 94 comprised of modules for communication with hardware components of the system over an application programming interface (API). The hardware components are the inter IC Bus (also known as the I2C-Bus, this component facilitates communication between electronic components), serial interface bus (SPI Bus), batteries, electronics, optional internal barcode reader and SD card.

As will be described further below, the software enables the apparatus to be operated in several modes, including a 'read now' mode where a test device inserted into the apparatus is immediately read; a 'walk away' mode where a test device inserted into the apparatus is incubated for a selected or predetermined period of time prior to being read; a mode to recall test results; a mode to recall control results. Accordingly, in one embodiment, the apparatus is designed to be operated in two or more, three or more or four or more modes.

Test Device: Exemplary Lateral Flow Immunoassay

Figure 8:
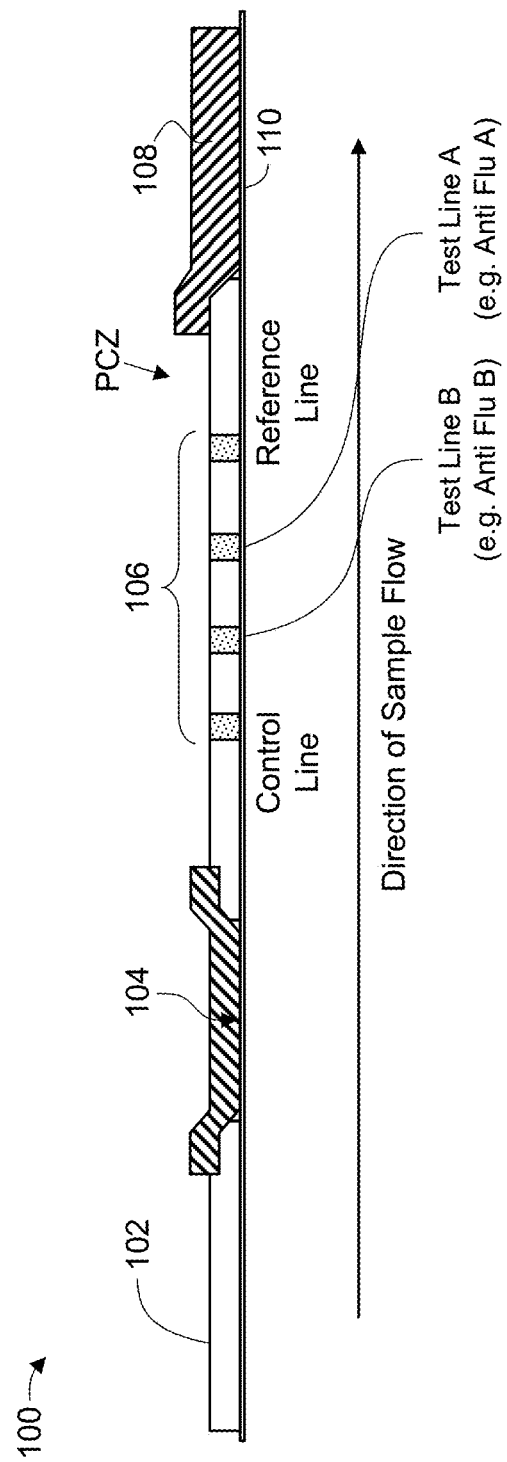
FIG. 8 is an illustration of an embodiment of a test device, exemplified by a lateral flow immunoassay.
Figure 9A:
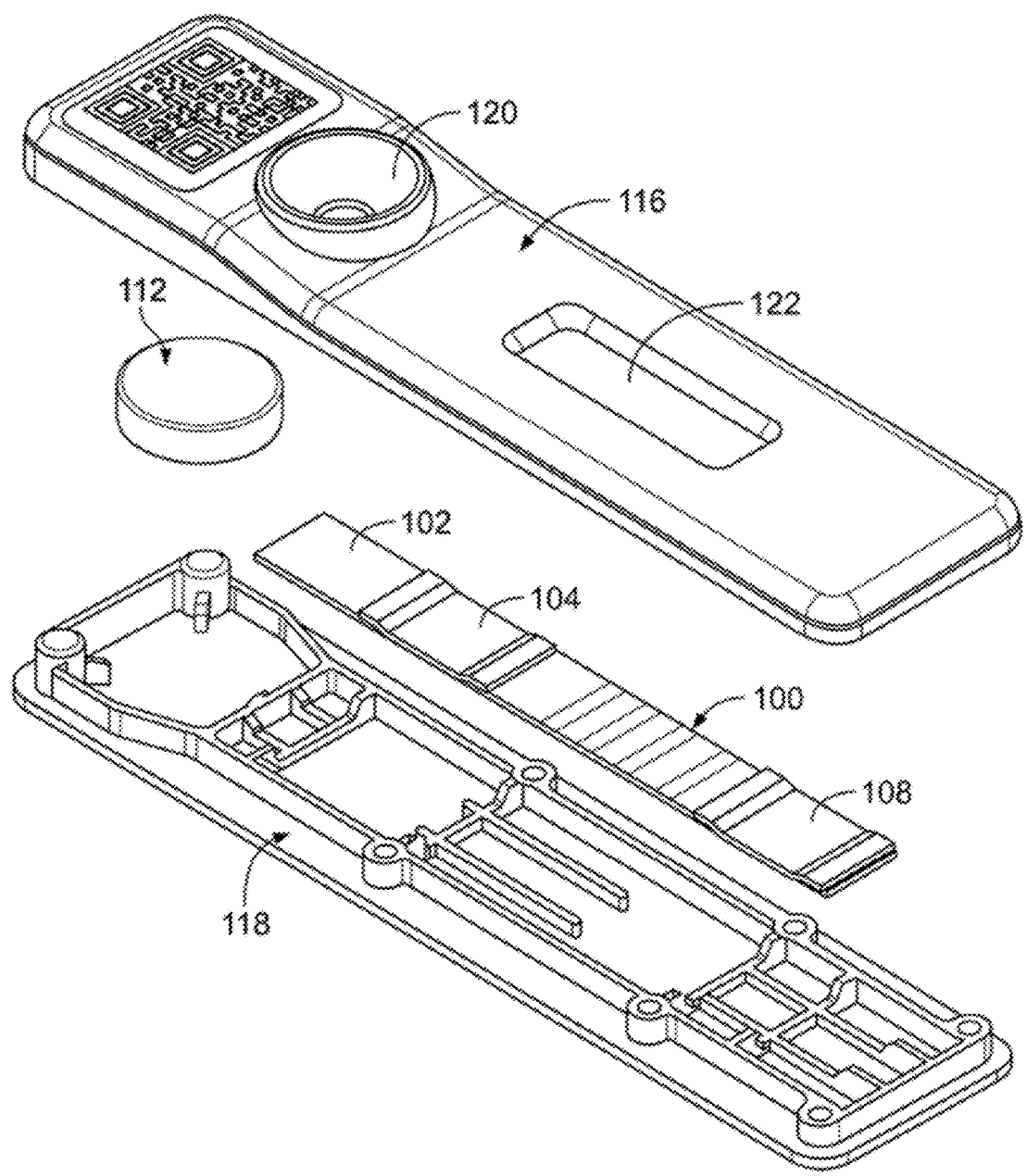
FIGS. 9A-9B are illustrations of a test device wherein a test strip is enclosed in an optional housing sized for insertion into a drawer of an apparatus.
Figure 9B:
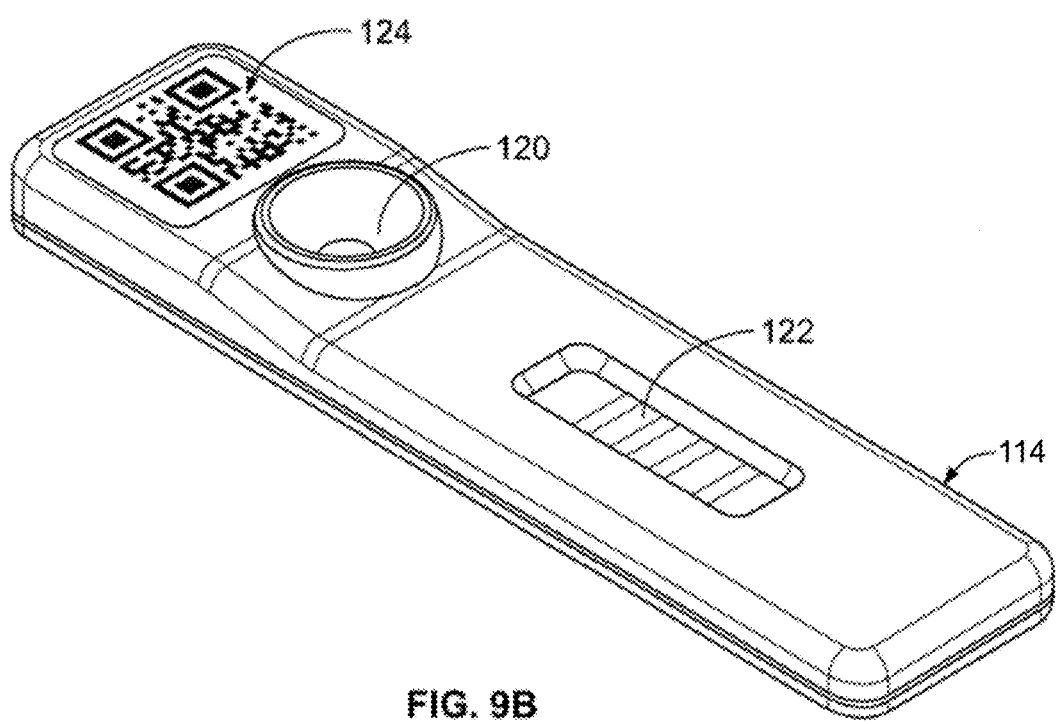

With reference to FIG. 8 and FIGS. 9A-9B, an embodiment of a test device for interaction with the apparatus is illustrated. The test device is exemplified in the drawings below by a lateral flow test immunoassay, however it will be appreciated that a lateral flow immunoassay is exemplary of test devices suitable for interaction with the apparatus. Test device 100 is comprised of, in sequence, a sample pad 102, a label pad 104, one or more lines indicated collectively at 106 and selected from a test line, a control line and a reference line, and an absorbent pad 108. In one embodiment, a support member 110 is provided, and each or some of the sample pad, label pad, lines and absorbent pad are disposed on the support member. As will be described below with reference to FIG. 10, the test device comprises a region between the downstream edge of the most downstream analyte-specific test line, which in the embodiment shown in FIG. 8 is test line for binding to an influenza antigen (e.g., a test line that comprises anti-flu A antibodies), and the upstream edge of the absorbent pad 108 is a procedural control zone, denoted PCZ in FIG. 8. In some embodiments, the test device additionally includes a desiccant portion, not shown in FIG. 8, but visible in an embodiment shown FIG. 9A. A desiccant portion can be positioned on the support member of the test device, and in one embodiment is disposed on the support member downstream of the absorbent pad, as described in U.S. Patent Application Publication No. 2008/0311002, incorporated by reference herein. In another embodiment, seen in FIG. 9A, a desiccant portion 112 is a discrete component, physically separate from the test strip, inserted into a housing member that contains the test strip.

In one embodiment, the test strip is enclosed in a housing, sometimes referred to as a cassette, such as housing 114 in FIG. 9B. Optional housing 114 in this embodiment is comprised of an upper member 116 and a lower member 118 that fit together to form a housing. Lower member 118 may include architectural features that define dimensioned regions for receiving the test strip 110 and the optional desiccant 112. Upper housing member 116 includes at least two openings, a first sample input port 120 and a viewing window 122. The sample input port is disposed directly above the sample pad on the test strip, so that a sample dispensed into the sample input port contact the sample pad for flow along the test strip. In the embodiment shown, the sample input port includes a bowl portion to receive a liquid sample into the port. The viewing window is positioned to reveal the lines in the test strip, so the optics system in the apparatus can interact with the lines, as will be described below.

In the embodiment shown in FIG. 9B, a bar code label 124 is affixed to the upper housing member. It will be appreciated that the bar code label can be positioned elsewhere on the housing, and is positioned for interaction with the internal bar code scanner positioned within the apparatus. In one embodiment, the bar code label is a 2D bar code, encoding information, for example, regarding the assay test strip, such as the pathogen/analyte the test strip is designed to detect (Flu A/B, Strep A, RSV, others listed below, etc.) which informs the apparatus what protocol in memory to initiate for scanning the test strip; a unique test serial number so that the apparatus will not read same test strip twice. In one embodiment, the information contained in the bar code does not include information related to the patient or the sample type, and is limited to information about the test strip.

It will be appreciated that the test device illustrated in FIGS. 8-9 is exemplary of lateral flow test devices in general. The test strip can be configured uniquely for any given analyte, and the external housing is optional, and if present, need not be a cassette housing but can be a flexible laminate, such as that disclosed in U.S. Patent Application Publication No. 2009/02263854 and shown in Design Patent No. D606664, which are both incorporated by reference herein. The system requires only that the drawer in the apparatus and the test device be dimensioned to receive the test device in the drawer, and the optics system in the apparatus have a movement path the scans the necessary regions of the test device.

Figure 10:
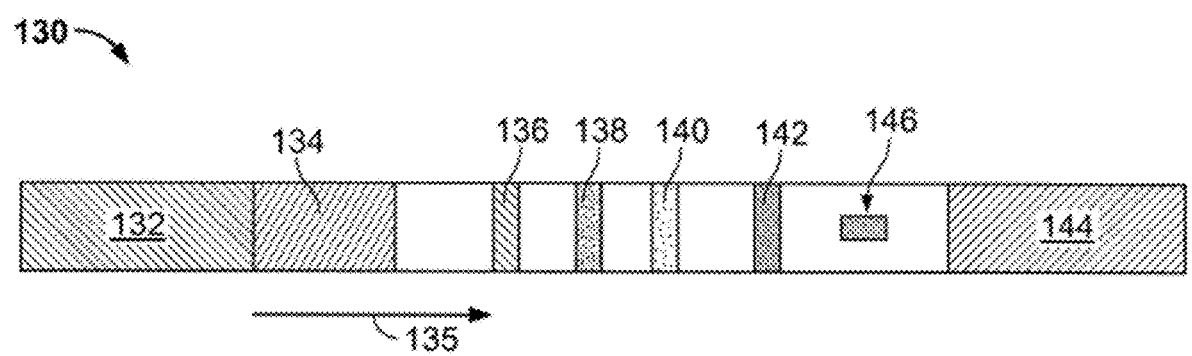
FIG. 10 is a top view of an exemplary test device and the arrangement of its structural and immunochemical features for interaction with the apparatus.

In that regard, FIG. 10 is a top view of an exemplary test strip and the arrangement of its structural and immunochemical features for interaction with the apparatus. Test strip 130 includes a sample receiving zone 132 in fluid communication with a label zone 134. A fluid sample placed on or in the sample zone flows by capillary action from the sample zone in a downstream direction, indicated by arrow 135. Label zone 134 is in fluid communication with at least a test line and a control line or a reference line. In the embodiment shown in FIG. 10, the label zone is in fluid communication with a negative control line 136, an analyte test line 138, an optional second analyte test line 140, a reference line 142. The two or more lines are in fluid communication with an absorbent zone 144. That is, the label zone is downstream from the sample zone, and the series of control and test lines are downstream from the label zone, and the absorbent pad is downstream from the portion of the test strip on which the lines are positioned. A region between the downstream edge of the most downstream analyte-specific test line, which in the embodiment shown in FIG. 10 is test line 140, and the upstream edge of the absorbent pad is a procedural control zone (PCZ) 146. Reference line 142 is within the procedural control zone 146. As will be described below, the procedural control zone, and in particular the reference line therein, (i) ascertains whether sample flow along the test strip occurred based on its RLU signal (emission), and (ii) is used by the algorithm to determine the relative locations of the other lines (control, if present, and analyte-specific test line(s)) on the test strip. Materials for construction of each of the zones is well known in the art, and includes, for example, a glass fiber material for the sample zone, a nitrocellulose material on which the two or more lines are positioned.

The sample zone receives the sample suspected of containing an analyte of interest control its flow into the label zone. The label zone, in one embodiment, contains two dried conjugates that are comprised of particles containing a lanthanide element. The lanthanide materials include the fifteen elements lanthanum, cerium, praseodymium, neodymium, promethium, samarium, europium, gadolinium, terbium, dysprosium, holmium, erbium, ytterbium, lutetium, and yttrium. In one embodiment, the particles are polystyrene particles or microparticles (particles less than about 1,000 micrometers in diameter, preferably less than about 500 micrometers in diameter, more preferably less than 200, 150 or 100 micrometers in diameter) containing a luminescent or fluorescent lanthanide, wherein in one embodiment, the lanthanide is europium. In a preferred embodiment, the lanthanide is a chelated europium. The microparticles, in one embodiment, have a core of a lanthanide material with a polymeric coating, such as a europium core with polystyrene coating. A binding partner for the analyte(s) of interest in the sample is/are attached to or associated with the outer surface of the microparticles. In one embodiment, the binding partner for the analyte(s) of interest is an antibody, a monoclonal antibody or a polyclonal antibody. A skilled artisan will appreciate that other binding partners can be selected, and can include complexes such as a biotin and strepavidin complex. Upon entering the label zone, the liquid sample hydrates, suspends and mobilizes the dried microparticle-antibody conjugates and carries the conjugates together with the sample downstream on the test strip to the control or reference and test lines disposed on the nitrocellulose strip. If an analyte of interest is present in the sample, it will bind to its respective conjugate as the specimen and microparticles flow from the label zone onto the surface of the nitrocellulose. In the embodiment shown in FIG. 10, this flowing mixture will then encounter negative control line 136. The negative control line is comprised of mouse immunoglobulin (IgG) and enables detection of non-specific binding of the conjugates to the immunoglobulin, thus approximating the level of non-specific binding that will occur at the downstream test line(s). The signal generated at this negative control line is used to help ensure that high non-specific binding at the analyte-specific test line does not lead to false positive results.

As the sample and microparticle-antibody conjugates continue to flow downstream, if antigen is present in the sample, the fluorescent microparticle-antibody conjugate which now includes bound with antigen/analyte of interest, will bind to the test line(s). In some embodiments, a single test line is present on the test strip. In other embodiments, at least two, or two or more test lines are present on the strip. By way of example, and as detailed in Example 1, a test strip intended for detection and/or discrimination of influenza A and influenza B will include a first test line to detect influenza A and a second test line to detect influenza B. Microparticle-antibody conjugates comprised of microparticles coated with antibodies specific for influenza A and microparticles coated with antibodies specific for influenza B are included in the label zone. A first test line for influenza A and a second test line for influenza B are disposed downstream of the label zone, and preferably downstream of the negative control line. The first test line for influenza A comprises a monoclonal or polyclonal antibody to a determinant on the nucleoprotein of influenza A and the second test line for influenza B comprises a monoclonal or polyclonal antibody to a determinant on the nucleoprotein of influenza B. If antigen is present in the sample, a typical immunoassay sandwich will form on the respective test line that matches the antigen in the sample.

The microparticle-antibody conjugates that do not bind to the negative control line or to a test line continue to flow by capillary action downstream, and the remaining sample encounters the reference line. The reference line is comprised of goat anti-mouse immunoglobulin, and at least a portion of microparticle-antibody conjugates that reach the reference line will bind non-specifically to the goat anti-mouse immunoglobulin. Fluorescent signal generated at this line provides information, for example, about the flow of the sample and also can serve as a location marker to direct the apparatus to the precise other locations on the nitrocellulose that are to be scanned by the optics system, as will be described below. The remaining sample then flows downstream of the reference line into the procedure control zone 146 that is also scanned by the optics system and is used, for example, to confirm that adequate flow of the sample has occurred. The sample with any remaining microparticle-antibody conjugate then flows on into the absorbent pad.

III. Test Procedure and System Operation

As mentioned above, the apparatus can be operated in two modes, a 'read-now' mode or a 'walk-away' mode. The flow of sample from deposition on the sample pad to the absorbent pad takes between 2-20 minutes, more typically between 5-18 minutes, more typically between 7-15 minutes. A user can opt to place the sample on the sample pad of the test device, insert the test device into the drawer of the apparatus, and set the apparatus in 'walk-away mode' whereupon the apparatus will scan the bar code on the test device and determine the correct incubation time for the test device that permits sufficient time for the sample to flow from the sample pad to the absorbent pad. Alternatively, a user can opt to place the sample on the sample pad of the test device and incubate the test device external the apparatus. The test device is then inserted into the drawer of the apparatus subsequent to an incubation period external to the apparatus, and a user can operate the apparatus in 'read-now' mode wherein the apparatus will scan the bar code on the test device to determine the assay type and immediately initiate the scanning protocol for that assay type. The scanning protocol and the processing of information from a scan will now be described, with reference to FIGS. 11-12.

A. Operation of Apparatus

Figure 11:
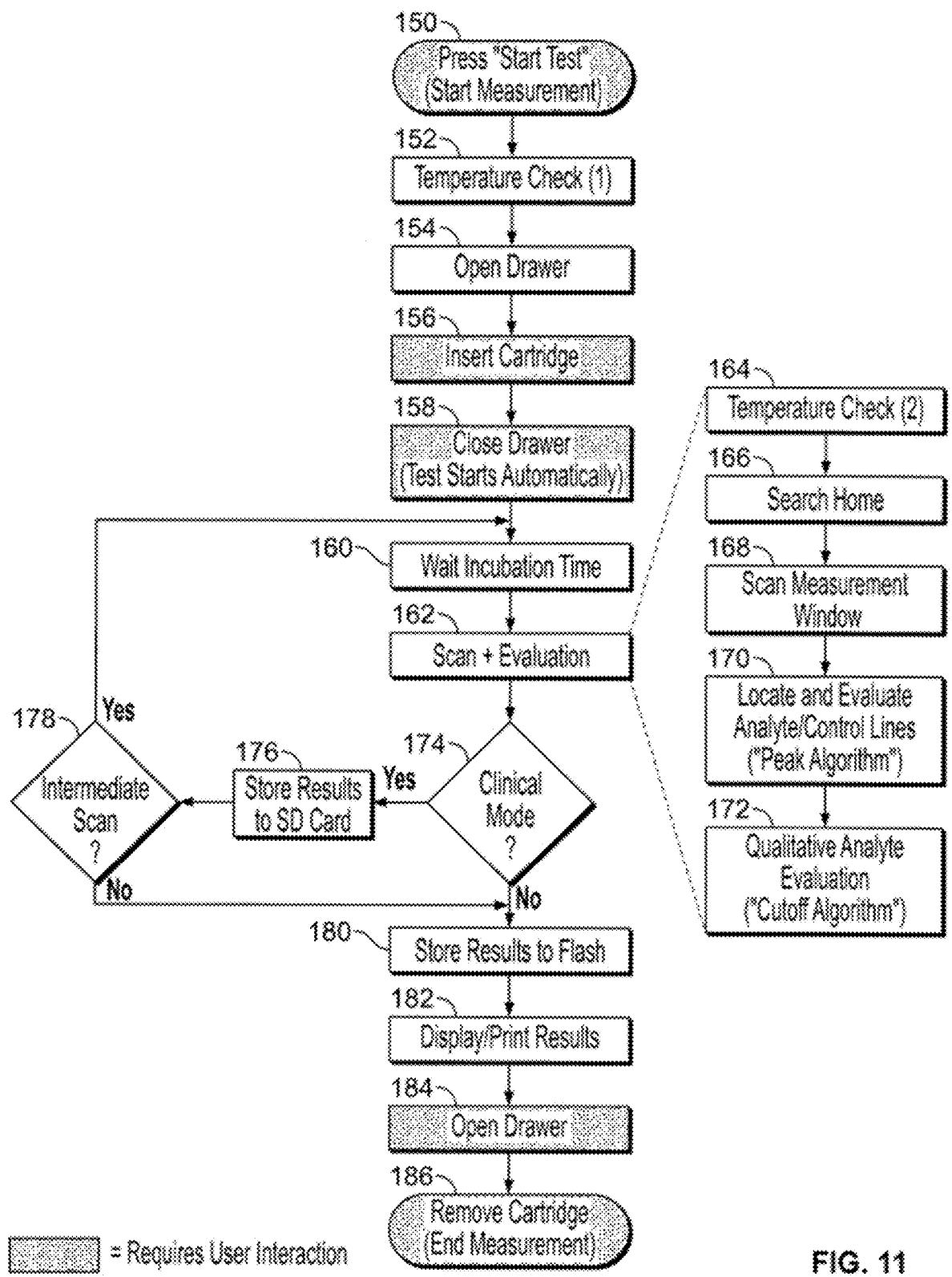
FIG. 11 shows the sequence of events in one embodiment of a measurement procedure where an apparatus as described herein interacts with a test device.

To initiate a scan of a test device, the apparatus is powered-on if needed and the toggle switch to initiate the apparatus software is activated. Prior to inserting the test device with sample into the apparatus, using the optional external bar code reader information about the user, the sample, the patient, etc. can be scanned into the apparatus memory. With reference to FIG. 11, a "start test" button on the apparatus or on the touch screen is pressed, 150, to start a measurement of a test device. The apparatus takes a temperature reading, 152, and then automatically opens the drawer in the apparatus, 154, to receive the test device on which a sample has been dispensed onto the sample pad. The test device with loaded sample is inserted into the drawer, 156, and the drawer is closed manually, 158, with gentle pressure by the user. As the drawer closes, one or more positioning arms press against the test device to position it in the drawer in a precise location that is consistent from test to test. The optics shield within the apparatus is positioned to protect the optics system and its movable optics module from any liquid sample that may splash from the sample input port when the drawer closes.

Closure of the drawer initiates a sequence of events, 158, comprised of the following. The internal bar code reader scans the bar code on the test device and receives information regarding the assay type (e.g., influenza A/B, Strep A, RSV, etc.), the serial number and the expiration date of the test device, optical cut-off information for the assay type, and any other information included on the bar code secured to the test device. In one embodiment, a mirror is positioned to facilitate interaction of the light beam from the internal bar code scanner and the bar code label on the test device. It will be appreciated that the internal bar code reader is an optional feature, as the information on the bar code label can be entered into the apparatus by a user using the key pad or via an external bar code scanner. Based on the test assay type discerned from the information on the bar code label or otherwise provided to the apparatus processor, the apparatus initiates an algorithm stored in the apparatus' memory for the assay for which the test device is designed, and based on user defined selection of read-now mode or walk-away mode, a protocol stored in memory initiates. In walk-away mode the apparatus incubates for a period of time, 160, prior to initiating a scan of the test device, 162; in read-now mode the apparatus does not wait for the preset incubation time for that particular assay, and immediately begins a scan of the test device, 162.

The scan and evaluation of the test device, 162, comprises another temperature check, 164, at the same or different position from the first temperature check 152. The initiated algorithm activates the optics system, including the stepper motor that moves the optics module with respect to the test device that is stationary in the apparatus. The optics system searches for its home position, 166, (described below) and then conducts a scan of the measurement window, 168, in the housing of the test device through which the reference/control and test lines are visible. The motor in the optics system moves the optics module incrementally from a defined start point along the length of the measurement window in the test device in accord with parameters defined by the algorithm for the particular assay being conducted. As will be described in more detail below, the optics module is moved in incremental steps by the motor in the optics system along the length of the test window, in a downstream to upstream direction with respect to sample fluid flow on the test strip, wherein the optics carriage stops at each incremental step or position to illuminate the position, detect emitted light after illumination at that position, before advancing upstream to the next position.

After collection of emitted light at each of the plurality of incremental positions along the length of the test window, the algorithm locates and evaluates the data in the data array that is associated with the control lines, 170, and conduct a qualitative analyte evaluation using a cut-off algorithm, 172.

The algorithm then determines whether the test is a clinical test, an external control or a calibration test, 174, and if the determination is yes (based on information provided on the test device bar code or based on user input information), the results are stored to memory, 176, such as on the SD card or in the apparatus memory. An intermediate scan 178 may be performed after the results are stored on the SD card. If the test is not a clinical test, then results are stored to flash memory, 180, and displayed and/or printed, 182. The drawer is then opened, 184, by the apparatus or by the user at the end of the measurement sequence for the user to remove the test device, 186.

Figures 12A, 12B:
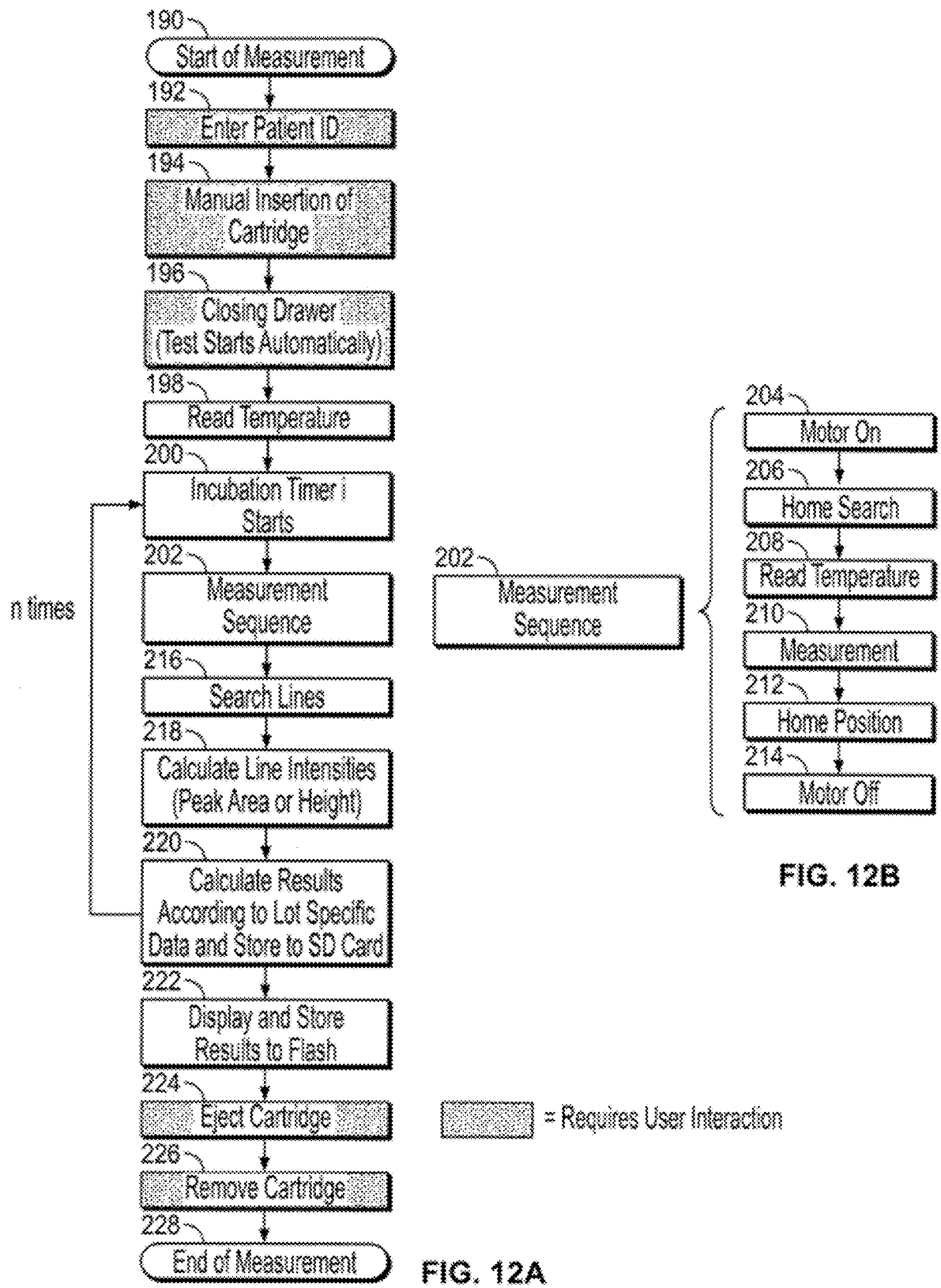
FIGS. 12A-12B show the sequence of events in another embodiment of a measurement procedure where an apparatus as described herein interacts with a test device.

FIGS. 12A-12B shows a second exemplary test sequence for the apparatus described herein. It will be appreciated that the test sequence is easily varied by simply varying the programming in the software programs in the device, to alter the sequence of events, time allocated to each event, etc., in a measurement procedure. In the exemplary procedure of FIGS. 12A-12B, start of the measurement procedure is initiated, 190, by pressing a button or switch on the apparatus. Information regarding the patient (name, gender, age, etc.) is entered, 192, by the user via entry using the keypad on the apparatus or via an external bar code scanner. The drawer in the apparatus is opened using a button on the apparatus and the test device is inserted into the drawer, 194. Closing of the drawer manually or automatically by the apparatus initiates an automated sequence of events, 196. The sequence includes reading the temperature at one or more locations inside the apparatus, such as adjacent the test window, and/or taking an ambient temperature reading, 198. If an incubation time is commanded by a user selecting 'walk-away' mode or by a pre-programmed requirement for a particular test assay, an incubation time starts, 200. Upon completion of the incubation time or if no incubation time is required or commanded, the measurement sequence by the optics system automatically initiates, 202.

With reference now to FIG. 12B, the measurement sequence by the optics system includes activating the motor that moves the optics module, 204, and the optics module finding its home position, 206. A temperature reading, 208, in the vicinity of the optics system can be taken. At a first position along the optical read path that corresponds with the test window on the test device inserted in the apparatus, the illumination source in the optics module is turned on and then off, and during the off period fluorescent emission is detected by the photodetector in the optics module. The detected emission is stored in memory, and the motor in the optics system advances the optics module a fixed amount to its next position, which in an embodiment is in a direction toward the sample zone in the device so that measurement of the lines in the test window occurs in a downstream to upstream direction with respect to fluid flow on the test strip. After completion of a predefined number of incremental steps along the length of the test window and capture of light emission at each step, 210, the optics module is returned to its home position by the motor, 212, and the motor is powered off, 214. It will be appreciated from this description that, in one embodiment, the apparatus comprises a dynamic optics module of an illumination source and a photodetector, wherein the module is static during an illumination/detection sequence and resumes dynamic movement thereafter. It will also be appreciated that the dark reading, i.e, detected emission during the off, or dark period, of the illumination-detection sequence, is utilized for purposes of baseline and background and not for time-resolved fluorescence.

The algorithm stored in apparatus memory for that particular assay then searches the data array for the peak emissions for each of the test, control, reference lines, 216, to calculate line intensities of peak area or peak height, 218. The algorithm calculates results from the data array, 220, and stores the results to memory, such as on the SD card inserted into the device. The calculated result can be displayed to the screen on the apparatus, or prompted to be printed by the user, or stored in flash memory if needed, 222.

A user can then instruct the apparatus to open the drawer, to remove the test device, 224, 226, ending the measurement procedure, 228.

In one embodiment, and with specific reference to a test device like that shown in FIG. 10 for detection and/or discrimination of two analytes in sample, such as influenza A and influenza B, the strip is incubated in the apparatus when operated in walk-away mode for approximately fifteen minutes, at which time the apparatus initiates an optical scan of the test device, measuring fluorescence signals across the strip's length and performs calculations and reports the test results. The scanning of the test device strip and analysis requires less than about 60 seconds, and more preferably is between about 20-60 seconds, more preferably 30-45 seconds.

The apparatus, the test device, and the test procedure wherein the two interact, has several built-in control features to ensure that the correct result will be reported apparatus. A first feature is the location of the reference line on the test device, which is used by the algorithm to determine the relative locations of the other control and analyte-specific test lines on the test device. The software program expects the reference line to be located within a specific, pre-defined location range. The acceptable range for the location of the reference line is based on the manufacturing tolerance for placement of immunochemistry on the test strip, for location of the test strip within the housing, and for positioning of the test device (test strip in the housing (cassette)) within the drawer of the apparatus. Once the reference line is located, the positions of each of the other test lines and zones are determined by the algorithm and match the locations of the various chemistries deposited on the test strip.

Figure 13A:
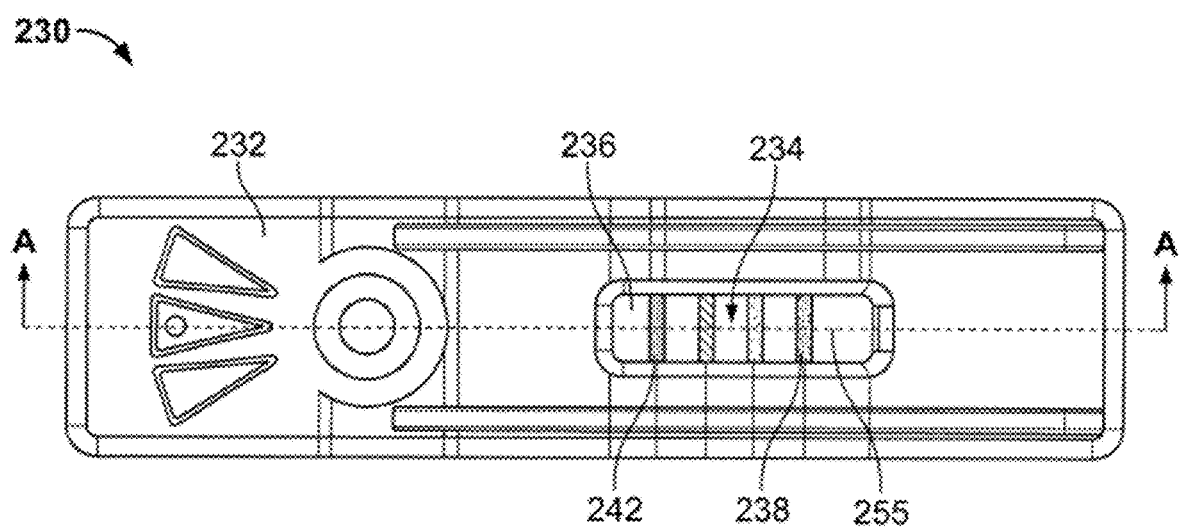
FIGS. 13A-13C correspond to a top view of a test device (FIG. 13A), a cross-sectional view of the test window region of the test device (FIG. 13B), and an exploded view of a portion of a test device showing an embodiment of the arrangement of test lines, reference lines and control lines on a test device (FIG. 13C)
Figure 13B:
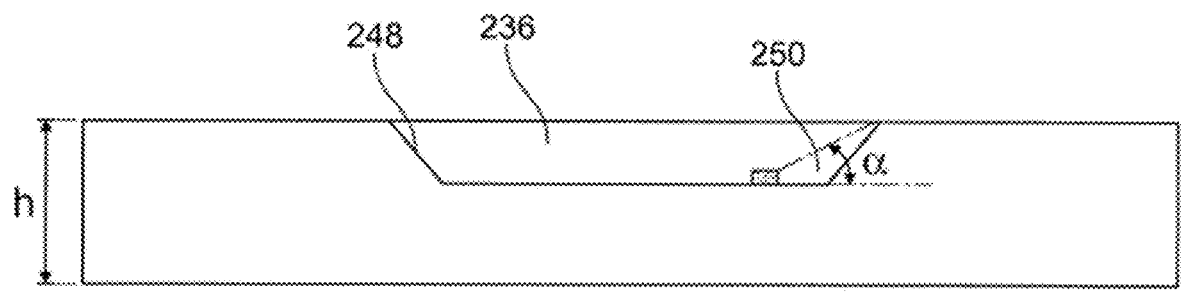
Figure 13C:
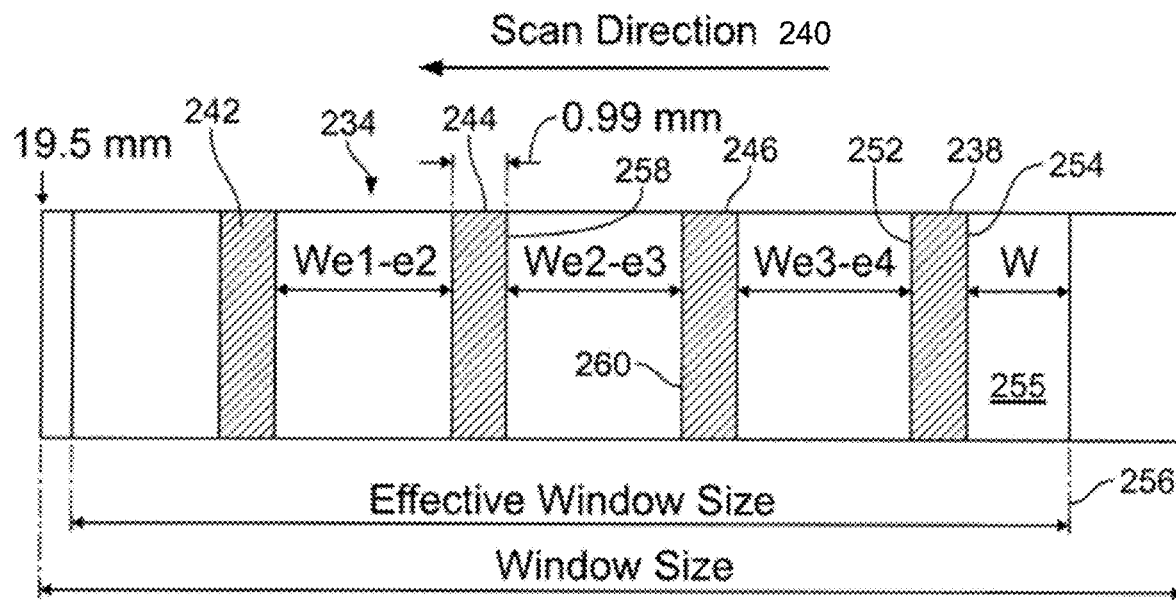

More specifically, and with reference to FIGS. 13A-13C, a top view of a test device 230 is shown, the test device having an external housing 232. Inserted inside the housing is a test strip 234, seen partially in FIG. 13A through the window 236 in the housing. The portion of test strip 234 comprising the at least one control or reference line and at least one test line, also referred to herein as the "nitrocellulose region" of the test strip, is shown in FIG. 13C. A reference line 238 on the test strip is the distal most line on the test strip, relative to the proximal end of the test strip where the sample pad is positioned. That is, the reference line is the line furthest downstream (with respect to the direction of sample fluid flow) on the test strip. Because the optics system scans the nitrocellulose region visible through the test window in the housing in a downstream to upstream direction, as indicated by arrow 240 in FIG. 13C, where downstream to upstream is relative to sample fluid flow on the test strip, the reference line is the first line encountered with the optics system initiates its scan of the test device. As mentioned above, the reference line is comprised of, for example, goat anti-mouse polyclonal antibody, or another antibody that provides non-specific binding. The reference line serves two purposes. First, the reference line's relative fluorescence units (RFU) signal desirably exceeds a specified minimum (such as 1,000 RFUs) in order to demonstrate adequate sample flow, otherwise the test is interpreted as invalid. The minimum RLU is information that can be provided on the bar code for each test device or is information stored in memory. It will be appreciated that the minimum RLU for a reference line in a test strip may be assay specific, where the minimum RLU for a test device for Strep A may be different than the minimum RLU for a test device that detects RSV. Second, the location of the reference line peak in the data array enables the use of an algorithm to locate the other test lines on the test strip, and specifically in the nitrocellulose region, thereby specifying the scanning locations for the other test lines.

The test strip also includes, in some embodiments, a negative control line 242. The negative control line is comprised of normal mouse immunoglobulin (IgG), and provides two functions. The negative control line enables measurement of the level of non-specific binding of the microparticle-antibody conjugates, thereby approximating the level of nonspecific binding that will occur on the test line(s). The negative control line also serves as an indicator of adequate incubation time and sample flow; e.g. if the RLU signal for the negative control line exceeds a specified maximum, adequate flow has not yet occurred and the assay is interpreted as invalid.

The test strip also includes at least one analyte-specific test line. In embodiments where two or more analytes are to be detected and discriminated, two or more test lines are provided. In one embodiment, such as the embodiment illustrated in FIG. 13A and FIG. 13C, the test strip comprises two analyte-specific test lines, for example, a first line 244 with monoclonal antibodies to the nucleoprotein of influenza A and a second line 246 with monoclonal antibodies to the nucleoprotein of influenza B. These analyte-specific test lines serve to capture the fluorescent microparticle-antibody conjugates when in the presence of their corresponding, respective antigens.

The tolerance between lines (analyte-specific, reference and control) on the test strip is precise, so that the optics module illuminates directly above a middle region of the lines. The reference line in some embodiments is wider that the other lines on the test strip, to give the optics module a larger target for finding its point of reference. It will be appreciated that the lines require a certain minimum spacing to avoid overlap of peak emission so that a baseline can be determined between each line. As seen in FIG. 13B, which shows a cross-section of the window of a test device, the angle of the wall 248 of the test window 236 creates a shadow 250. The shadow decreases the actual window length to an effective window length. The reference line 238 has a certain width $w_{ref}$, that in one embodiment is larger than the width $w_{test}$, of an analyte-specific test line. The reference line has an upstream edge 252 and a downstream edge 254, with respect to the direction of fluid flow on the test strip. A procedural control zone 255 is defined by the downstream edge 254 of the reference line and the downstream end 256 of the effective window length. In one embodiment, the dimensional width of the procedural control zone 255 is less than the width between lines upstream of the reference line. For example, in the embodiment shown in FIG. 13C, test line 244 has a downstream edge 258 and test line 246 has an upstream edge 260. The distance between edges 258 and 260 defines a width, $w_{l1 \to l2}$, between lines upstream of the reference line, and in one embodiment this width, $w_{l1 \to l2}$, is greater than the width of the procedural control zone. The spacing $w_{l1 \to l2}$, between two lines in the nitrocellulose region of the test strip, is determined in conjunction with the shape of the beam of light from the LED such that a dark space between test lines where no emissivity signal occurs. This ensures a baseline is detected between each peak emission from the sequential, adjacent test lines.

The optics system in the apparatus is an assembly of mechanical, electronic and optical components which serves to illuminate the test strip with an ultraviolet light-emitting diode (UV LED) and then collects, processes and transforms the resulting europium fluorescence signal using a photodiode to an electronic signal that is converted by an analogto-digital converter into useable analytical data. The LED is a semiconductor device which emits light (UV at 365 nm in one embodiment), and during a measurement procedure the LED is pulsed on and off at each incremental step of the optics system along the optical path defined by the test window. The resulting fluorescence emission is collected by a photodiode during and between illumination pulses. The unprocessed signal is manipulated by subtracting the background signal (LED off) from the signal with the LED on. The optic system collects signal data expressed in RFUs from each of the lines (reference, test, and control), when the optics module is positioned at one of is plurality of incremental positions along the length of the nitrocellulose region on which the plurality of lines are disposed. In one embodiment, the dwell time of the optics module at each incremental step is on the order of 2000-8000 microseconds, more generally between 3000-4500 microseconds. It will be appreciated that the dwell time at each step can be varied to manipulate sensitivity of the assay, where a longer dwell time at each step will increase sensitivity, and dwell time can be decreased to decrease overall test time.

At end of a scan of lines in the window, the data collected consists of emission signals from the test strip at the position when LED is on (365 nm) and emission signals from test strip at that position when LED is off. The difference between these values at each position is taken, and stored in memory as a one-dimensional array of the difference in emissivity at each position when LED is on and when LED is off. The data processing algorithm smooths the data array using a local polynomial regression (of degree k) on the series of differential emissivity values equally spaced in the series (such as the Savitzky-Golay method), to determine a smoothed value for each point. In one embodiment, the algorithm smooths 13 points in the array, and the first derivative of the smoothed data array is taken, and the peak/trough of the derivative peak height is determined to be the cut-off value. In other embodiments, the apparatus is programmed to analyze the resulting signal data in a way that will yield qualitative results. The programming involves a cut-off value that corresponds to an analyte-specific RFU signal that is first defined by the apparatus' algorithm and then used to help calculate a positive or negative result. The signal to cut-off ratio corresponds to a simple ratio of the signal in RFUs obtained at each test line divided by its cutoff where the specimen giving any S/CO value ≥1 is positive and any S/CO value <1 is negative. Signal data that is collected is processed using a Savitzky-Golay smoothing algorithm that uses a weighted average smoothing method that reduces unwanted electronic noise, while preserving actual test signals, including maxima, minima and peak width with little impact on their actual dimensions.

In one embodiment, a negative control threshold is provided on the bar code information for each test device. The negative control threshold is a test strip lot-specific RFU value that impacts the calculation of the cut-off. For example, when the RFU of the negative control exceeds the negative control threshold value, then the cutoff calculation is changed from a fixed cutoff of 675 RFUs to a cutoff based on multiplying the RFU of the negative control value found on each test strip by a lot-specific correction factor. In another embodiment, a dual positive threshold value is provided for each test device, which corresponds to an RFU level used to determine the clinical outcome for a sample when the RFU signals for antigen A (e.g., influenza A) and for antigen B (e.g., influenza B) are both above their respective cutoffs—i.e. when a dual positive result is obtained. After the cutoffs for antigens A and B are determined, the RFU value of the antigens A and B test line signals are compared to this dual positive threshold value. Depending upon this comparison, a special algorithm may be triggered to calculate a positive or negative test result.

Figure 14A:
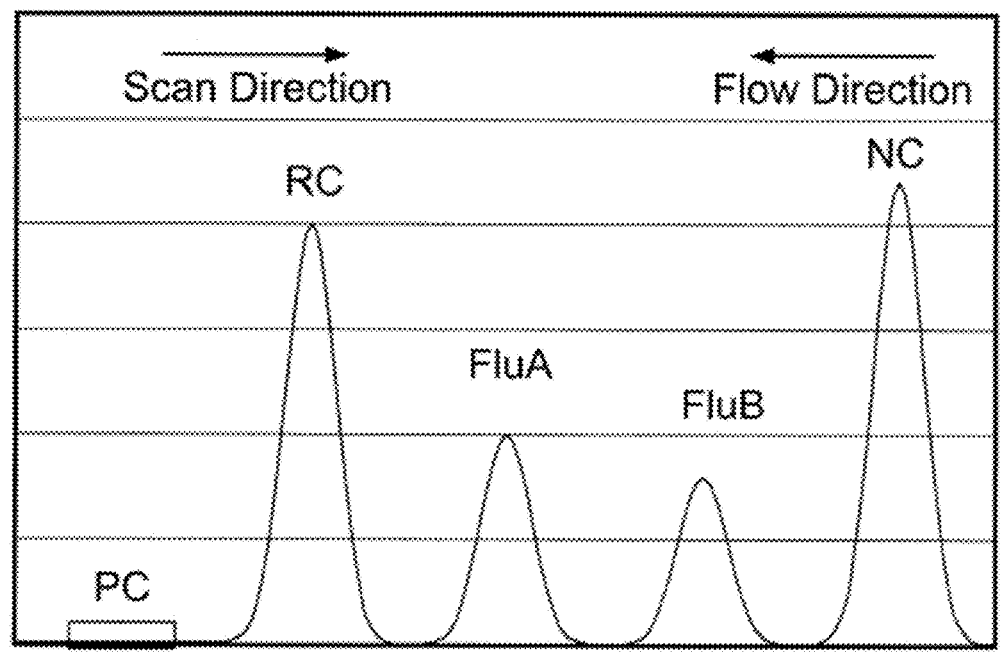
FIGS. 14A-14C are graphs showing an exemplary data set from an optical scan of a test device for detection of influenza A and influenza B, where the data is shown in arbitrary RLU as a function of position of the optics module (FIG. 14A), and the signal peak for the reference control line is presented as the first derivative to illustrate functioning of the algorithm to determine whether a peak is a maximum and not a minimum (FIG. 14B) and to determine peak height (FIG. 14C).
Figure 14B:
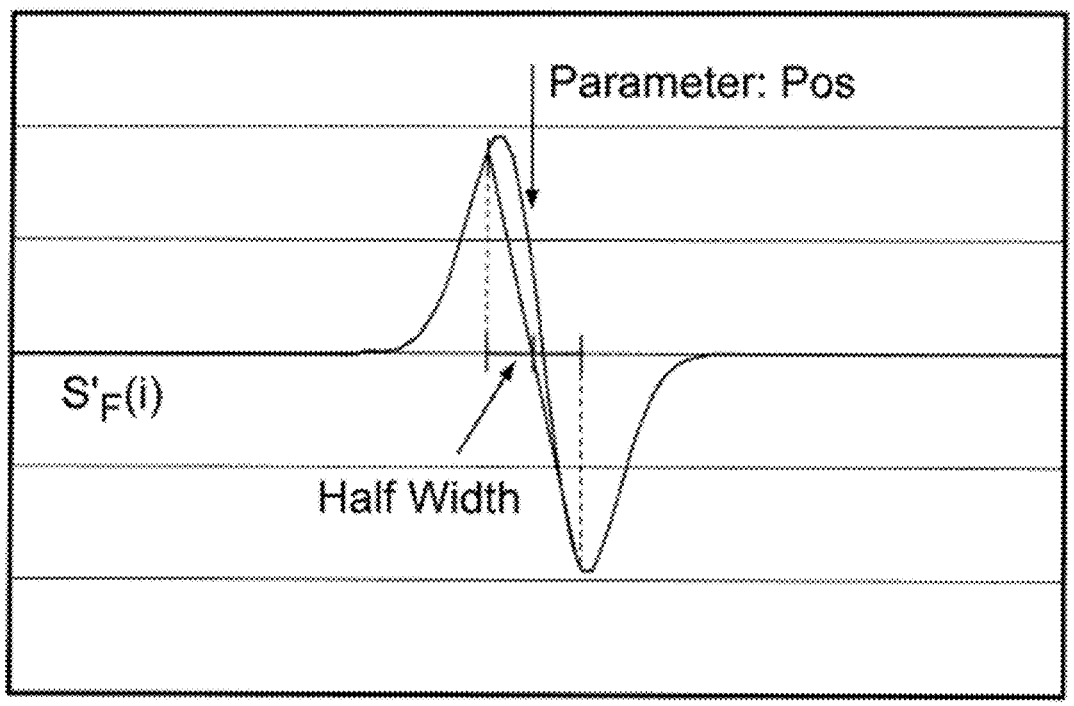
Figure 14C:
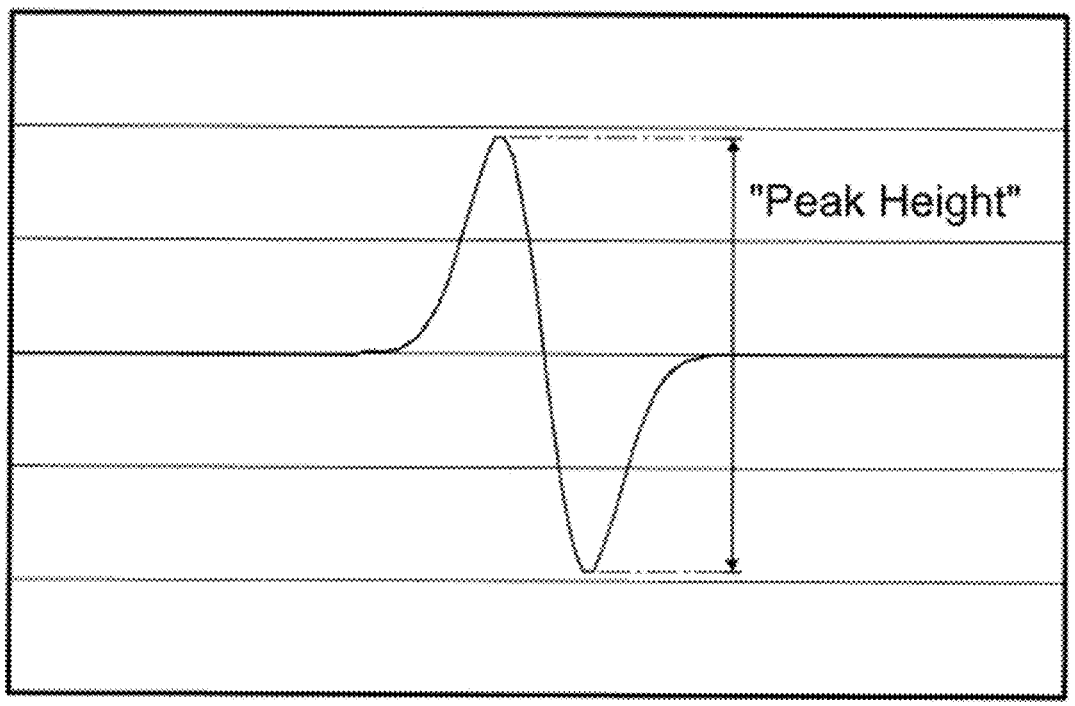

FIGS. 14A-14C are graphs showing an exemplary data set from an optical scan of a test device for detection of influenza A and influenza B. Upon completion of a scan of the test strip, a signal differential is determined for each incremental position by taking the difference between the signal detected during the illumination measurement where the LED is on (s(i)$_{illum}$) and the signal detected during dark measurement where the LED is off (s(i)dark). This 'dark-corrected signal', s(i)DC, at each position i is calculated by:

$$sDC = sillum - sdark$$

The dark-corrected signal is checked for consistency by testing the condition:

$$sDC(i) > \text{MinDarkCorrCounts for all } i$$

where MinDarkCorrCounts corresponds to the minimal allowed value for the dark corrected signal. Conversion of signal index (i) to a position x in mm is done by:

$$x_{(i)} = x_{start} + \Delta x \cdot i$$

$$i_{(x)} = \text{roundtonearest}(x - x_{start}/\Delta x)$$

where $x_{start}$ is the start position of the scan, x is the distance between two samples of the signal in mm.

Signal preparation is done by smoothing the signal and calculating the first derivative. Both the smoothed signal and the derivative of the smoothed signal are used as input parameters for a peak analysis. The first line in the scan, which corresponds to the reference line, is the position reference line for the other lines on the test strip. The reference line has a wider search range than the other lines, giving it a larger tolerance. Based on this positional control, the expected position (x) of the other peaks in the data set is known. The algorithm conducts a polarity check on the derivative of the peaks corresponding to the analyte-specific test line and control lines, to determine if the peak is a maximum and not a minimum. As seen in FIG. 14B, the derivative of a positive peak (maximum) has a maximum, a zero crossing, and a minimum. The polarity check considers two points of the derivative; one is located half peak width (expected) left of the (expected) peak center; the other is half peak width right to center. If these points are connected by a straight line, this line must have a negative slope. A polarity check of the reference line is not done, as the positional tolerance for the reference control line is high. The next step in peak detection is searching for a maximum and a minimum in the derivative, which is illustrated in FIG. 14B. Then, a peak height can be calculated, as shown in FIG. 14C. The algorithm calculates the peak height against a baseline, and if the peak height is greater than a cutoff value, the analyte is present and a positive result is reported.

In summary, the apparatus and test device described herein include several features that are uniquely interactive to provide a sensitive, specific system. The test device includes a label pad with particles or micro-beads having a fluorescent material, and coated with antibodies with specific binding affinity for an analyte of interest. The test device includes a procedural control located after the last analyte-specific test line on the test strip. The procedural control zone is a region located between the last analyte test line and the absorbent pad. The analyzer scans this zone positioned at the downstream end of the test device, and determines whether adequate flow of the sample has occurred. A minimum and maximum fluorescent signal specification for this procedural control zone is one of the fail safe features incorporated into the assay. No colored test or procedural control lines will be visible to the human eye in the test window of the fluorescent assay cassette. The apparatus automatically scans the test strip, collects and analyzes the fluorescence data, and then calculates and reports the result. These features eliminate the subjectivity required to interpret results in visually human-read lateral flow assays. In addition, a negative control line located on the test strip, downstream of the label pad, and before an analyte specific test line. This negative control line serves as another procedural control and also as a source of information for calculating each assay's cutoff. The assay's sensitivity is derived from the use of a unique polystyrene microbead that has been dyed with a chelate of europium. The europium compound (more than $1 \times 10^6$ fluorescent molecules per bead) that is encased within the microbeads is temperature stable, resistant to bleaching in room light, and yields a very efficient conversion of the UV energy from 365 nm to a wavelength of 618 nm. This large Stokes shift protects against many naturally occurring fluorescent compounds that may be present in the test materials and/or clinical specimens.

B. Assays and Analytes to be Detected

The system comprised of an apparatus and a test device as described herein is intended for detection of any analyte of interest. Analytes associated with a disorder or a contamination are contemplated, including biological and environmental analytes. Analytes include, but are not limited to, proteins, haptens, immunoglobulins, enzymes, hormones, polynucleotides, steroids, lipoproteins, drugs, bacterial antigens, viral antigens. With regard to bacterial and viral antigens, more generally referred to in the art as infections antigens, analytes of interest include *Streptococcus*, Influenza A, Influenza B, respiratory syncytial virus (RSV), hepatitis A, B and/or C, pneumoccal, human metapneumovirus, and other infectious agents well known to those in the art.

In other embodiments, a test device intended for detection of one or more of antigen associated with Lyme disease, In another embodiment, a test device designed for interaction with the apparatus is intended for use in the field of women's health. For example, test devices for detection of one or more of fetalfibronectin, chlamydia, human chorionic gonadotropin (hCG), hyperglycosylated chorionic gonadotropin, human papillomavirus (HPV), and the like, are contemplated.

The test devices are intended for receiving a wide variety of samples, including biological samples from human bodily fluids, including but not limited to nasal secretions, nasopharyngeal secretions, saliva, mucous, urine, vaginal secretions, fecal samples, blood, etc.

The test devices, in one embodiment, are provided with a positive control swab or sample. In another embodiment, a negative control swab or sample is provided. For assays requiring a external positive and/or negative control, the apparatus is programmed to request a user to insert into the apparatus a test device to which a positive control sample or a negative control sample has been deposited. Kits provided with the test device can also include any reagents, tubes, pipettes, swabs for use in conjunction with the test device.

IV. Examples

The following examples are illustrative in nature and are in no way intended to be limiting.

Example 1

Detection and Discrimination of Influenza A and B

A lateral flow test device comprised of a test strip and a housing was prepared. The test strip was fabricated to have a sample pad comprised of a glass fiber matrix in fluid connection with a nitrocellulose strip, one or both supported on a support membrane.

Using standard NHS/carboxyl chemistry, specific monoclonal antibodies were covalently bound to the surface of europium chelate (β-diketone)-incorporated polystyrene beads to form fluorescent microparticle-antibody conjugates. The microparticle-antibody conjugates were deposited on a glass fiber matrix to form a label pad. The label pad was positioned adjacent the sample pad in a downstream direction. Two populations of microparticle-antibody conjugates coated with uniquely different monoclonal antibodies, one with monoclonal antibody directed to influenza A nucleoprotein and a second with monoclonal antibody directed to influenza B nucleoprotein, were prepared and deposited in the label pad.

An absorbent pad comprised of a highly absorptive material that acts as a wick to draw fluid from the nitrocellulose strip, thereby helping to ensure that adequate sample flow through the entire test strip was achieved, was positioned on the test strip downstream from the label pad and the nitrocellulose region.

The test strip was secured in a housing, for ease of handling. On an external upper surface of the housing was a bar code label containing information about the test strip, including for example, the intended analyte to be detected (influenza A and influenza B), a device specific identification number, and an expiration date.

A nasal swab sample from a patient presenting with flu symptoms was treated with a reagent solution to form a test mixture. A portion of the test mixture was dispensed onto the sample pad via the sample input port in the housing.

Using the external barcode reader, the user scanned the patient information into the apparatus or enters the information using the keypad on the apparatus. The user selected walk-away mode and inserted the test device into the drawer of the apparatus. After an incubation time of 15 minutes, the apparatus initiated its measurement sequence to scan the test device. The internal bar code scanner read the information on the bar code label on the test device to determine the assay type, the device lot number, the test device serial number and the test device expiration date. The microprocessor loaded the correct program into memory for the assay type to be run.

The microprocessor-controlled optics unit in the apparatus conducted its incremental, step by step scan of the length of the viewing window, which approximately corresponds to the length of the nitrocellulose region on the test strip. On the nitrocellulose strip the lines were sequentially read, beginning with the most downstream line, the reference line. The optics module moved relative to the stationary test device in an upstream direction to each of the analyte-specific test lines. At each incremental step, UV light from the UV LED with a peak emission at 365 nm was flashed on and then off. The UV light excited the europium fluorophore which in turn emitted light at a wavelength of 618 nm.

After the apparatus completed its optical scan of the test window on the test device and collected the fluorescent data, it objectively interpreted the assay result. There were five possible results: (1) positive for influenza A and negative for B; (2) positive for influenza B and negative for A; (3)

positive for both influenza A and B; (4) negative for both influenza A and B; and (5) invalid. A positive result for either analyte was determined by detection of a fluorescent signal at levels above a signal threshold set upon scanning the negative control line by a specific algorithm in the apparatus. The fluorescence signal obtained with this assay was invisible to the unaided eye, and indicated the test sample was positive for influenza A and negative for influenza B. The test result can only be obtained with a fluorescent analyzer, which afforded fully objective interpretation of the test result.

Example 2

Detection and Discrimination of Influenza A and B

The purpose of this study was to determine the stability of influenza A and B viruses stored for up to 72 hours at different temperatures in different viral transport media as shown by subsequently testing in the apparatus. Saline and eight (8) different commercially available viral transport media (VTM) were evaluated in this study. One influenza A and one influenza B isolate were used. Five different apparatuses were used. The study spanned a period from zero up to 72 hours. The performance of the various VTMs was evaluated at two different controlled temperatures.

The following materials were used in this study: (1) Consumable Materials in Table 2-1; (2) Biological Materials in Table 2-2; (3) five different apparatuses; and, (4) software.

testing. This study examined the performance of the test devices and the apparatus when testing samples diluted and stored in different Viral Transport Media (VTMs) at different temperatures. The study demonstrated the stability of the viruses themselves when stored in different VTMs for up to 72 hours at two different temperatures.

Some clinics use saline instead of commercial VTMs for transport or temporary storage of patient specimens. Influenza A and B virus dilutions were therefore prepared in saline. Each dilution contained a final test concentration 2 to 3 times the LoD for the respective viruses. Sufficient volumes were prepared to complete testing at each time point. The dilution scheme used for the influenza A and influenza B virus is shown in Table 2-3.

Preparation of Virus Dilutions in Viral Transport Media (VTM)

The Influenza A and B virus dilutions were separately prepared in various types of VTM. Each dilution contained a final test concentration 2 to 3 times above the predetermined LoD. The final reconstituted extraction reagent contained 260 µL of saline and 260 µL of virus diluted in different VTMs. Sufficient volumes were prepared to complete testing at each time point. Dilutions of each virus were prepared in the following media: M5, M4, M4-RT, UTM, M6, Hank's Balanced Salts, Starplex Multitrans, and Modified Liquid Stuart's.

TABLE 2-1

Consumable Materials

| Description | Part Number | Lot Number | Expiration Date |
|---|---|---|---|
| Influenza A + B Test Cassettes | 1169100 | 2010-1501 | TBD |
| Reagent Tube | 1170700 | 2010-1267 | TBD |
| Pipette, Transfer, 120 uL, 25/Bag | 1184000 | TBD | TBD |
| Saline (also Reagent Solution) | 0107000 | 815959 | Sep. 30, 2013 |
| Media, Micro-Test M5 | 1187900 | 954506 | Apr. 4, 2012 |
| Media, Micro-Test M4 | 1189800 | 029462 | Oct. 2, 2012 |
| Media, Universal Viral Transport | 1189900 | 10A135 | Oct. 31, 2012 |
| Media, Micro-Test M4-RT | R12505 Remel | 015638 | Aug. 30, 2012 |
| Media, Micro-Test M6 | R12530 Remel | 951531 | Mar. 26, 2012 |
| Media, Hank's Balanced Salts | 10-508F BioWhittaker | 203205 | Oct. 18, 2012 |
| Media, Starplex Multitrans | S160-FL Starplex | 106H39 | September 2012 |
| Modified Liquid Stuart's Media | SP132-FL Starplex | 1C14A | Sep. 14, 2012 |
| Control Positive Swab | 1168500 | 2010-1289 | TBD |
| Control Negative Swab | 1053300 | 201613 | May 8, 2013 |

TABLE 2-2

Influenza Viruses

| Virus Strain | TCID50/mL |
|---|---|
| A/Hong Kong/8/68 | 6.1 × 106 |
| B/Allen/45 | 4.2 × 105 |

The five apparatuses used in the study were identified by the following serial numbers: Analyzer S/N 213; Analyzer S/N 217; Analyzer S/N 219; Analyzer S/N 225; Analyzer S/N 231.

Methods

Viral Transport Media are used to stabilize patient specimens when they are being transported or stored prior to

TABLE 2-3

Dilution Scheme for Influenza Viruses

| Influenza Virus | Virus Dilution # | Virus Dilution # Used | Vol. Virus (mL) | Vol. Diluent (mL) | Conc. (TCID50/mL) | Final Vol. (mL) |
|---|---|---|---|---|---|---|
| A/Hong Kong/8/68 | 0 | NA | NA | NA | 6.11E+06 | NA |
|  | 1 | 0 | 0.016 | 4.984 | 20000 | 5.000 |
|  | 2 | 1 | 0.448 | 39.552 | 224 | 40.000 |
| B/Allen/45 | 0 | NA | NA | NA | 4.20E+05 | NA |
|  | 1 | 0 | 0.095 | 1.905 | 20000 | 2.000 |
|  | 2 | 1 | 0.180 | 39.820 | 90 | 40.000 |

General Procedure

The Influenza A+B test assay was performed as described in Example 1 and in accord with the package insert. The positive and negative External Controls were tested on each day of the study. The apparatus was used in the Read Now mode throughout the study. All data were stored on a SD card located in each apparatus; this SD card was removed and the data were extracted after the testing was completed.

Experimental Protocol

Testing with Saline

Saline without added virus was tested for each condition in replicates of 5 (n=5); 520 µL of the saline were added into the extraction reagent tube and mixed according to the package insert. This volume was used in order to mimic the same conditions that are employed when testing with specimens suspended in VTM as well nasopharyngeal aspirate and wash samples. Next, 120 µL of the reconstituted extraction reagent was added to the test cassette, using the kit's transfer pipette. The test cassette was incubated for 15 minutes on the benchtop and analyzed using the Read Now mode. A new extraction tube was rehydrated for each test.

All virus dilutions prepared in saline were stored at RT or at 2-8° C. and tested in replicates of 5 (n=5) at the following time points: 0 hrs, 2 hrs, 4 hrs, 6 hrs, 24 hrs, 48 hrs, and 72 hrs. To test the virus dilutions that had been prepared in saline, 260 µL of the saline were added into the extraction reagent tube. Then, 260 µL, of the virus diluted in saline were added into the extraction reagent tube and mixed according to the package insert. Next, 120 µL of the reconstituted extraction reagent was added to the test cassette, using the kit's transfer pipette. The test cassette was incubated for 15 minutes on the benchtop, using the Read Now mode and analyzed. A new extraction tube was rehydrated for each test.

Testing with Viral Transport Media

The VTMs containing no spiked virus were tested at time zero only. Ten replicates (n=10) of these unspiked VTM samples were tested. There were two temperature conditions evaluated for each medium: RT and 2-8° C. To test the unspiked VTMs, 260 µL of the saline and 260 µL, of the appropriate VTM were added into the extraction reagent tube and mixed. Next, 120 µL of the reconstituted extraction reagent was added to the test cassette, using the kit's transfer pipette. The test cassette was incubated for 15 minutes on the benchtop, using the Read Now mode and analyzed. A new extraction tube was rehydrated for each test.

All VTMs spiked with virus were tested in replicates of 5 (n=5) at the following time points: 0 hrs, 2 hrs, 24 hrs, 48 hrs, and 72 hrs. Specimens were stored at two different temperature conditions, RT and 2-8° C., up to each time point for each of the prepared dilutions. To test the spiked VTMs, 260 µL of the saline, followed by 260 µL of the appropriate virus dilution in VTM were added into the extraction reagent tube and mixed according to the package insert. Next, 120 µL of the reconstituted extraction reagent were added to the test cassette, using the kit's transfer pipette. The test cassette was incubated for 15 minutes on the bench top using the Read Now mode and inserted in to the Sofia Analyzer for analysis. A new extraction tube was rehydrated for each test.

Results

The Influenza A and B results were reported as positive, negative or invalid for each virus dilution and condition. The results for each virus at each time point and for each temperature-challenging condition are presented in Tables 2-4, 2-5, 2-6, and 2-7.

TABLE 2-4

Stability of Influenza A* Stored in Saline and Various VTMs at 2-8° C.

Number of Positive Results for Influenza A**

| Media | T = 0 hrs | T = 2 hrs | T = 4 hrs | T = 6 hrs | T = 24 hrs | T = 48 hrs | T = 72 hrs |
|---|---|---|---|---|---|---|---|
| Saline | 5/5 | 5/5 | 5/5 | 5/5 | 5/5 | 5/5 | 4/5 |
| M4 | 5/5 | — | — | 5/5 | 4/4*** | 5/5 | 5/5 |
| UTM | 5/5 | — | — | 5/5 | 5/5 | 5/5 | 5/5 |
| M5 | 5/5 | — | — | 5/5 | 5/5 | 5/5 | 5/5 |
| M6 | 5/5 | — | — | 5/5 | 5/5 | 5/5 | 5/5 |
| M4-RT | 5/5 | — | — | 5/5 | 5/5 | 5/5 | 5/5 |
| Starplex | 5/5 | — | — | 5/5 | 5/5 | 5/5 | 5/5 |
| Hank's | 5/5 | — | — | 5/5 | 5/5 | 3/5 | 1/5 |
| Stuart's | 5/5 | — | — | 5/5 | 1/5 | 0/5 | 0/5 |

*The influenza A strain used was A/HK/8/68 (TCID50/mL = 224).
**There were no false positives for influenza B and no invalid results under any condition.
***One replicate was mistakenly not tested.

TABLE 2-5

Stability of Influenza A* Stored in Saline and Various VTMs at 25° C.

Number of Positive Results for Influenza A**

| Media | T = 0 hrs | T = 2 hrs | T = 4 hrs | T = 6 hrs | T = 24 hrs | T = 48 hrs | T = 72 hrs |
|---|---|---|---|---|---|---|---|
| Saline | 5/5 | 5/5 | 5/5 | 4/5 | 5/5 | 1/5 | 0/5 |
| M4 | 5/5 | — | — | 5/5 | 5/5 | 5/5 | 5/5 |
| UTM | 5/5 | — | — | 5/5 | 5/5 | 5/5 | 5/5 |
| M5 | 5/5 | — | — | 5/5 | 5/5 | 5/5 | 5/5 |
| M6 | 5/5 | — | — | 5/5 | 5/5 | 5/5 | 5/5 |
| M4-RT | 5/5 | — | — | 5/5 | 5/5 | 5/5 | 5/5 |
| Starplex | 5/5 | — | — | 5/5 | 5/5 | 5/5 | 5/5 |
| Hank's | 5/5 | — | — | 5/5 | 4/5 | 0/5 | 0/5 |
| Stuart's | 5/5 | — | — | 0/5 | 0/5 | 0/5 | 0/5 |

*The influenza A strain used was A/HK/8/68 (TCID50/mL = 224).
**There were no false positives for influenza B and no invalid results under any condition.

TABLE 2-6

Stability of Influenza B* Stored in Saline and Various VTMs at 2-8° C.

Number of Positive Results for Influenza B**

| Media | T = 0 hrs | T = 2 hrs | T = 4 hrs | T = 6 hrs | T = 24 hrs | T = 48 hrs | T = 72 hrs |
|---|---|---|---|---|---|---|---|
| Saline | 5/5 | 5/5 | 5/5 | 5/5 | 5/5 | 4/5 | 0/5 |
| M4 | 5/5 | — | — | 5/5 | 5/5 | 5/5 | 5/5 |
| UTM | 5/5 | — | — | 5/5 | 5/5 | 5/5 | 5/5 |
| M5 | 5/5 | — | — | 5/5 | 5/5 | 5/5 | 5/5 |
| M6 | 5/5 | — | — | 5/5 | 5/5 | 5/5 | 5/5 |
| M4-RT | 5/5 | — | — | 5/5 | 5/5 | 5/5 | 5/5 |
| Starplex | 5/5 | — | — | 5/5 | 5/5 | 5/5 | 5/5 |
| Hank's | 5/5 | — | — | 5/5 | 5/5 | 5/5 | 2/5 |
| Stuart's | 5/5 | — | — | 5/5 | 5/5 | 0/5 | 0/5 |

*The influenza B strain used was B/Allen/45 (TCID50/mL = 90).
**There were no false positives for influenza A and no invalid results under any condition.

TABLE 2-7

Stability of Influenza B* Stored in
Saline and Various VTMs at 25° C.

| Media | Number of Positive Results for Influenza B** | | | | | | |
|---|---|---|---|---|---|---|---|
| | T = 0 hrs | T = 2 hrs | T = 4 hrs | T = 6 hrs | T = 24 hrs | T = 48 hrs | T = 72 hrs |
| Saline | 5/5 | 5/5 | 5/5 | 5/5 | 2/5 | 1/5 | 0/5 |
| M4 | 5/5 | — | — | 5/5 | 5/5 | 5/5 | 5/5 |
| UTM | 5/5 | — | — | 5/5 | 5/5 | 5/5 | 5/5 |
| M5 | 5/5 | — | — | 5/5 | 5/5 | 5/5 | 5/5 |
| M6 | 5/5 | — | — | 5/5 | 5/5 | 5/5 | 5/5 |
| M4-RT | 5/5 | — | — | 5/5 | 5/5 | 5/5 | 5/5 |
| Starplex | 5/5 | — | — | 5/5 | 5/5 | 5/5 | 5/5 |
| Hank's | 5/5 | — | — | 5/5 | 4/5 | 0/5 | 0/5 |
| Stuart's | 5/5 | — | — | 3/5 | 0/5 | 0/5 | 0/5 |

*The influenza B strain used was B/Allen/45 (TCID50/mL = 90).
**There were no false positives for influenza A and no invalid results under any condition.

CONCLUSION

Several different VTMs and saline were analyzed for their suitability to store influenza A and B viruses. Two different temperature conditions were examined, including ambient RT and 2-8° C. The stability of viruses that were stored in VTM or saline for 0 hours, 2 hours, 4 hours, 6 hours, 24 hours, 48 hours and 72 hours of incubation at 2-8° C. and RT was examined in the Influenza A+B test device. The study demonstrated that viruses stored in M4, UTM, M5, M6, M4-RT and Starplex Multitrans for up to 72 hours at either temperature still gave 100% correct results. Saline was not useable beyond 4 hours at RT, however, it could be used for up to 24 hours, if the sample were stored at 2° C. to 8° C. Hank's and Stuart's were inferior and not recommended for storing specimens at RT. However, Hank's can be used for storing specimens up 24 hours and Stuart's up to 6 hours at 2° C. to 8° C. All the media were shown to be compatible with the Influenza A+B test device; none gave false positive or invalid results under the conditions examined. All studies were done in full accord with the package insert carefully describes the procedure for testing samples suspended in VTM.

Example 3

Fluorescent Immunoassay Showing Improved Sensitivity for Detection of Respiratory Syncytial Virus (RSV Current Respiratory Syncytial Virus (RSV) rapid tests are visual, subjective tests which claim sensitivity of 83%-95% versus culture. Using the apparatus described herein, instrument-mediated interpretation of the test result eliminates the subjectivity and difficulties sometimes encountered with traditional visually-interpreted, rapid tests. The study described in this example illustrates the improved detection of RSV using the apparatus. The extraction reagent provided with a lateral flow immunoassay test kit for detection of RSV was rehydrated, the nasopharyngeal swab containing a sample was placed into the extraction reagent and an aliquot of the extracted specimen was transferred onto the test cassette, which was then placed into the apparatus. All other steps for analysis and interpretation of the results were performed by the apparatus.

The analytical sensitivity of the RSV detection on the apparatus was compared to that of the visually-interpreted QuickVue® RSV 10 dipstick test. Five different strains of RSV (two type A and three type B) were diluted in M5 media to concentrations that yielded an optical density on the QuickVue visual test that non-technical readers have been demonstrated to interpret as positive 95% of the time. These dilutions were considered to be the Limits of Detection (LoD) for the respective strains on the QuickVue RSV 10 test. From these concentrations, additional dilutions of 1:100, 1:150, 1:200, 1:300, and 1:400 were made in M5 media for each RSV strain and tested on the RSV immunoassay read on the apparatus. For each viral strain, the highest dilution from the QuickVue LoD that yielded 100% positive results (5/5) was considered to be the comparative LoD for the RSV immunoassay read on the apparatus.

The clinical specificity of the RSV immunoassay read on the apparatus was evaluated using 50 nasopharyngeal swab samples that were collected from 50 different asymptomatic donors. To be eligible for the study, donors were required to be free of the common symptoms of RSV infection, including runny nose, congestion, cough, and fever. Swabs were placed directly into the rehydrated extraction reagent within one hour of collection and tested in the Sofia RSV FIA according to standard package insert directions.

Results

In the analytical sensitivity study, the dilutions of each viral strain from the QuickVue RSV 10 LoD that yielded 100% positive results on the RSV immunoassay read on the apparatus were 1:200 for strain A-2 ($TCID_{50}$/ml: $1.14 \times 10^3$); 1:200 for strain A Long ($TCID_{50}$/ml: $2.87 \times 10^3$); 1:300 for strain B 9320 ($TCID_{50}$/ml: $3.3 \times 10^0$); 1:100 for strain B WV/14617/85 ($TCID_{50}$/ml: $3.19 \times 10^8$); and 1:400 for strain B Wash/18537/62 ($TCID_{50}$/ml: $1.1 \times 10^1$).

In the clinical specificity study, all 50 of the samples collected from asymptomatic donors exhibited negative results on the RSV immunoassay read on the apparatus. The RSV immunoassay read on the apparatus demonstrated 100 to 400 times improved analytical sensitivity compared to the visually-interpreted dipstick test. A limited clinical study of 50 freshly-collected nasopharyngeal swab specimens demonstrated specificity of 100%.

Example 4

Detection of Group A *Streptococcus* Via Fluorescent Immunoassay

A clinical study was conducted at six (6) distinct sites in various geographical regions within the United States and two (2) sites in Australia. Two (2) throat swabs were collected from 596 patients with symptoms suggestive of bacterial pharyngitis. One throat swab was transported on cold ice packs to a central Reference Laboratory, streaked on a sheep blood agar plate (SBA) and cultured for up to 48 hours. Immediately after streaking, this same swab was tested using a fluorescent immunoassay lateral flow test strip read in the apparatus described herein. The performance of the system (lateral flow immunoassay and apparatus) was determined by comparison of the rapid test result to the corresponding culture result. Bacterial cultures with 10 or more GAS-positive colonies in the first quadrant of the streak plate, and zero or more in the other three quadrants were considered culture-positive.

The other throat swab, collected from the same patient, was tested directly in the physician's office or clinic without streaking on SBA. The results were compared to culture obtained with the first swab.

The swab that was sent to the reference laboratory for culture showed a clinical sensitivity of 100% and a specificity of 97% when rare culture results (defined by fewer than 10 colonies on a culture plate) were excluded. The data set included 79 Group A *Streptococcus* culture-positive specimens, and 499 culture-negative specimens.

|  | Culture | |
|---|---|---|
|  | Pos | Neg |
| Sofia Pos | 79 | 17 |
| Sofia Neg | 0 | 482 |
| Total: | 79 | 499 |

Sens = 79/79 (100%) (95% C.I. 94-100%)
Spec = 482/499 (97%) (95% C.I. 95-98%)
PPV = 82%
NPV = 100%

| Culture Classification of Throat Swab Specimens and Corresponding Sofia Strep A FIA Results | |
|---|---|
| Culture Classification | Sofia Strep A FIA Result |
| Rare | 11/18 (61%) |
| 1+ | 9/9 (100%) |
| 2+ | 22/22 (100%) |
| 3+ | 29/29 (100%) |
| 4+ | 19/19 (100%) |

There were 18 rarer and six invalids; and these samples were excluded from the calculations of clinical accuracy. This clinical data showed comparable results to traditional culture methods.

Example 5

Comparison of the System with Cell Culture and PCR, for Detection of Influenza A and B A study was conducted to establish the clinical performance of the system described herein, of a lateral flow immunofluorescence assay for influenza A and B read using an apparatus. The performance of the system was compared to the results obtained using cell culture and PCR.

The lateral flow immunoassay for Influenza A+B FIA test and the Molecular A+B PCR assay were obtained from Quidel Corporation (San Diego, Calif.). The reference culture method used R-Mix-2™ shell vials supplied by Diagnostic Hybrids, Inc.

Fresh nasal/nasopharyngeal swab specimens from a total of 929 consented patients were included in this analysis. Compared to culture, the fluorescent immunoassay read using the apparatus yielded 96.3% sensitivity and 97.4% specificity for influenza A and 92.3% and 97.9%, respectively for influenza B. Compared to PCR, the fluorescent immunoassay read using the apparatus yielded 80.7% sensitivity and 99.3% specificity for influenza A and 86.1% and 97.8%, respectively for influenza B. The tables below show the performance of the fluorescent immunoassay read using the apparatus compared to the Ct counts obtained with the PCR-positive specimens for influenza A and B. For PCR-specimens with Ct counts ≤30, fluorescent immunoassay read using the apparatus detected 96% that were PCR positive for A and 98% that were PCR positive for B.

The fluorescent immunoassay read using the apparatus yield within 15 minutes objective results that demonstrate high clinical accuracy versus culture and PCR, and thus provide ample time at the point-of-care for valid, informed patient management decisions.

TABLE 5-1

| | Influenza A | | |
|---|---|---|---|
| | Sofia | | |
| PCR Ct | #/N Positive | % Positive | 95% CI |
| Ct ≤ 20 | 32/32 | 100.0 | 89.1 to 100 |
| Ct > 20 to ≤25 | 105/108 | 97.2 | 92.1 to 99.4 |
| Ct > 25 to ≤30 | 48/53 | 90.6 | 79.3 to 96.9 |
| Ct > 30 to ≤35 | 10/17 | 58.8 | 32.9 to 81.6 |
| Ct > 35 to ≤40 | 2/16 | 12.5 | 1.6 to 38.3 |
| Ct > 40 to ≤45 | 0/18 | 0 | 0.0 to 18.5 |

TABLE 5-2

| | Influenza B | | |
|---|---|---|---|
| | Sofia | | |
| PCR Ct | #/N Positive | % Positive | 95% CI |
| Ct ≤ 20 | 5/5 | 100 | 47.8 to 100 |
| Ct > 20 to ≤25 | 68/71 | 95.8 | 88.1 to 99.1 |
| Ct > 25 to ≤30 | 71/71 | 100.0 | 94.9 to 100 |
| Ct > 30 to ≤35 | 16/25 | 64.0 | 42.5 to 82.0 |
| Ct > 35 to ≤40 | 4/15 | 26.7 | 7.8 to 55.1 |
| Ct > 40 to ≤45 | 3/7 | 42.9 | 9.9 to 81.6 |

Example 6

Detection of Influenza A+B

A beta-site study to collect and test prospective clinical specimens was conducted in January 2011 to further evaluate the test system. Under IRB approval and informed consent, 98 subjects, all children, contributed nasopharyngeal aspirates for testing. One portion of the specimen was tested directly and the other was placed into VTM and then tested, giving a total of 196 test results. The specimen placed into VTM was also tested using standard DFA and culture methods; results were further compared to an in-house-validated RT-PCR method.

The results compared with culture for Influenza A showed a clinical sensitivity of 98% and a specificity of 95%, representing 41 Influenza A culture-positive specimens. For Influenza B, the results showed a sensitivity of 100% and a specificity of 99% with a total of 19 influenza B positive specimens. Relative to RT-PCR the Influenza A clinical sensitivity and specificity were 85% and 98%, respectively, and for Influenza B the clinical sensitivity and specificity were 100% and 98%, respectively.

Example 7

Detection of Community Acquired Respiratory Viruses

Twenty influenza viruses were serially diluted in normal saline and tested using the point-of-care apparatus described herein on an influenza rapid antigen test strip. The viruses tested consisted of 2 H1N1pdm viruses, 1 of each of the 16 HA subtypes of influenza A, and one of each of the two lineages of influenza B. Logarithmic serial dilutions were made for each virus and tested in triplicate. Samples were run using the nasal wash procedure for each assay (i.e. 340 µL of the diluted virus was added directly to the sample extraction reagent). Limits of detection were recorded as the dilution in which at least two of the three replicates were positive.

The limit of detection for all influenza A virus samples ranged from ranged from $10^{18}$ to $10^{3.55}$ TCID$_{50}$/mL in the multiplex influenza rapid antigen test. The multiplex assay showed good dilutional sensitivity for all 20 influenza types and subtypes tested (including both H1N1pdm strains, the Yamagata lineage influenza B strain, and seven additional influenza A strains).

TABLE 7-1

| Virus Name | Quick Vue Influenza A + B Test LOD | Fluorescent Flu A + B Test LOD (MCW Results) | Fluorescent Flu A + B Test LOD (Raw Results) |
|---|---|---|---|
| A/WI/629-9/2008 (H1N1) | $1.0 \times 10^{4.55}$ | $1.0 \times 10^{4.55}$ | $1.0 \times 10^{3.55}$ |
| A/WI/629-2/2008 (H3N2) | $1.0 \times 10^{2.8}$ | $1.0 \times 10^{2.8}$ | $1.0 \times 10^{2.8}$ |
| A/WI/629-D02473/2009 (H1N1pdm) | $1.0 \times 10^{3.55}$ | $1.0 \times 10^{3.55}$ | $1.0 \times 10^{2.55}$ |
| A/WI/629-D02312/2009 (H1N1pdm) | $1.0 \times 10^{3.8}$ | $1.0 \times 10^{3.8}$ | $1.0 \times 10^{2.8}$ |
| A/Mallard/NY/6750/78 (H2N2) | $1.0 \times 10^{3.8}$ | $1.0 \times 10^{3.8}$ | $1.0 \times 10^{2.8}$ |
| A/Anhui/01/2005(H5N1)-PR8-IBCDC-RG5 | $1.0 \times 10^{3.05}$ | $1.0 \times 10^{2.05}$ | $1.0 \times 10^{2.05}$ |
| A/Chicken/NJ/15086-3/94 (H7N3) | $1.0 \times 10^{3.55}$ | $1.0 \times 10^{2.55}$ | $1.0 \times 10^{2.55}$ |
| A/Chicken/NJ/12220/97 (H9N2) | $1.0 \times 10^{2.8}$ | $1.0 \times 10^{2.8}$ | $1.0 \times 10^{2.8}$ |
| B/Ohio/1/2005 (Victoria/2/87-like) | $1.0 \times 10^{2.8}$ | $1.0 \times 10^{2.8}$ | $1.0 \times 10^{2.8}$ |
| B/Florida/07/2004 (Yamagata/16/88-like) | $1.0 \times 10^{4.05}$ | $1.0 \times 10^{4.05}$ | $1.0 \times 10^{3.05}$ |
| A/Mallard/OH/338/86 (H4N8) | $1.0 \times 10^{3.55}$ | $1.0 \times 10^{3.55}$ | $1.0 \times 10^{3.55}$ |
| A/Chicken/CA/431/00 (H6N2) | $1.0 \times 10^{3.8}$ | $1.0 \times 10^{3.8}$ | $1.0 \times 10^{2.8}$ |
| A/Blue Winged Teal/LA/B194/86 (H8N4) | $1.0 \times 10^{2.8}$ | $1.0 \times 10^{2.8}$ | $1.0 \times 10^{2.8}$ |
| A/GWT/LA/169GW/88 (H10N7) | $1.0 \times 10^{3.05}$ | $1.0 \times 10^{3.05}$ | |
| A/Chicken/NJ/15902-9/96 (H11N9) | $1.0 \times 10^{3.55}$ | $1.0 \times 10^{4.55}$ | $1.0 \times 10^{3.55}$ |
| A/Duck/LA/188D/87 (H12N5) | $1.0 \times 10^{4.05}$ | $1.0 \times 10^{4.05}$ | $1.0 \times 10^{3.05}$ |
| A/Gull/MD/704/77 (H13N6) | $1.0 \times 10^{1.8}$ | $1.0 \times 10^{1.8}$ | $1.0 \times 10^{1.8}$ |
| A/Mallard/GurjevRussia/262/82 (H14N5) | $1.0 \times 10^{1.8}$ | $1.0 \times 10^{1.8}$ | $1.0 \times 10^{1.8}$ |
| A/Shearwater/Australia/2576/79 (H15N9) | $1.0 \times 10^{2.8}$ | $1.0 \times 10^{2.8}$ | $1.0 \times 10^{2.8}$ |
| A/Shorebird/DE/172/2006(H16N3) | $1.0 \times 10^{2.8}$ | $1.0 \times 10^{1.8}$ | $1.0 \times 10^{1.8}$ |

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

It is claimed:

1. An apparatus, comprising:
   a housing configured to receive a test device, wherein the test device comprises a reference line and an analyte-specific test line;
   an illumination source;
   a detector; and
   a processor comprising a software program for control of the illumination source and the detector and for processing data obtained from the detector;
   wherein the processor is configured to direct the apparatus to:
   (a) generate a one-dimensional data array of values corresponding to signal associated with the reference line and the analyte-specific test line in response to illumination by the illumination source,
   (b) use data in the data array corresponding to data from the reference line to identify a location of data in the data array that corresponds to the analyte-specific test line, and
   (c) analyze data in the data array that corresponds to the analyte-specific test line to report a result regarding presence or absence of an analyte at the analyte-specific test line.

2. The apparatus of claim 1, wherein the detector is a single-element photodetector.

3. The apparatus of claim 1, wherein the illumination source is a light emitting diode.

4. The apparatus of claim 3, wherein the light emitting diode emits light at about 365 nm.

5. The apparatus of claim 3, further comprising a power output that provides the light emitting diode with at least about 4 mW.

6. The apparatus of claim 1, further comprising a cellular component that provides wireless transmission of data.

7. The apparatus of claim 6, wherein the cellular component transmits the result obtained from analysis of the data in the data array.

8. The apparatus of claim 1, wherein the apparatus further comprises a port for connection with an external instrument.

9. The apparatus of claim 1, wherein the processor is configured to direct the apparatus to analyze data in the data array by calculating a first derivative of the data array to identify a minimum peak and a maximum peak corresponding to the reference line.

10. The apparatus of claim 1, wherein the processor is configured to direct the apparatus to analyze data in the data array by taking the first derivative of the data array to form a derivative data set, wherein a first maximal value in the derivative data set corresponds to a maximum signal from a reference line or a control line on the test device, and the position in the derivate data array of the first maximal value determines the position of data from the analyte-specific test line.

11. The apparatus of claim 1, wherein the detector detects signal emitted from the test device during illumination by the illumination source.

12. The apparatus of claim 11, wherein the emitted signal is emitted from a fluorescing lanthanide compound.

13. The apparatus of claim 12, wherein the fluorescing lanthanide compound is chelated europium.

14. The apparatus of claim 13, wherein the chelated europium is embedded in microparticles.

\* \* \* \* \*